US008133673B2

(12) United States Patent
Holliger et al.

(10) Patent No.: US 8,133,673 B2
(45) Date of Patent: *Mar. 13, 2012

(54) COMPARTMENTALIZED SELF TAGGING

(75) Inventors: Philipp Holliger, Cambridge (GB);
Vitor B. Pinheiro, Cambridge (GB)

(73) Assignee: Medical Research Council, London (GB)

( * ) Notice: Subject to any disclaimer, the term of this patent is extended or adjusted under 35 U.S.C. 154(b) by 39 days.

This patent is subject to a terminal disclaimer.

(21) Appl. No.: 12/690,577

(22) Filed: Jan. 20, 2010

(65) Prior Publication Data

US 2010/0184071 A1 Jul. 22, 2010

Related U.S. Application Data

(63) Continuation of application No. 11/417,449, filed on May 3, 2006, now Pat. No. 7,691,576, which is a continuation of application No. PCT/GB2004/004649, filed on Nov. 3, 2004.

(30) Foreign Application Priority Data

Nov. 3, 2003 (GB) .................................. 0325653.4

(51) Int. Cl.
  *C12Q 1/68* (2006.01)
(52) U.S. Cl. ........................................................ 435/6.1
(58) Field of Classification Search ........................ None
  See application file for complete search history.

(56) References Cited

U.S. PATENT DOCUMENTS

| 7,138,233 | B2 | 11/2006 | Griffiths et al. |
| 7,225,943 | B2 | 6/2007 | Yang et al. |
| 7,691,576 | B2 * | 4/2010 | Holliger et al. ................... 435/6 |
| 2003/0134349 | A1 | 7/2003 | Ma et al. |
| 2004/0005594 | A1 | 1/2004 | Holliger et al. |

FOREIGN PATENT DOCUMENTS

| EP | 1680516 | 4/2008 |
| WO | WO-98/23733 | 6/1998 |
| WO | WO-99/02671 | 1/1999 |
| WO | WO-00/04139 | 1/2000 |
| WO | WO-00/40712 | 7/2000 |
| WO | WO-02/22869 | 3/2002 |
| WO | WO-03/044187 | 5/2003 |
| WO | WO-2005/045015 | 5/2005 |
| WO | WO-2005/045072 | 5/2005 |

OTHER PUBLICATIONS

Anarbaev, et al., "Klenow fragment and DNA polymerase ?-primase fromserva calf thymus in water-in-oil microemulsions", Biochimica et Biophysica Acta (1998) 1384: 315-324.
Astatke et al., "A single side chain prevents Escherichia coli DNA polymerase I (Klenow fragment) from incorporating ribonucleotides," Proc. Natl. Acad. Sci. USA (1998) 95: 3402-3407.
Barnes, "PCR amplification of up to35-kb DNA with high fidelity and high yield from λ bacteriophage templates," Proc. Natl. Acad. Sci. USA (1994) 91: 2216-2220.
Doublie et al, "Crystal structure of a bacteriophage T7 DNA replication complex at 2.2 Å resolution," Nature (1998) 391: 251-158.
Eigen, et al., "Hypercycles and Compartments. Compartments Assists—but do not replace—Hypercyclic Organization of Early Genetic Information", J. Theor. Biol. (1980) 85: 407-411.
Eigen, M. et al., "The Hypercycle. Coupling of RNA and Protein Biosynthesis in the Infection Cycle of an RNA Bacteriophage", Biochemistry (1991) 30: 11005-11018.
Embleton et al., "In-cell PCR from mRNA: amplifying and linking the rearranged immunoglobulin heavy and light chain V-genes within single cells," Nucleic Acids (1992) 20: 3831-3937.
Ghadessy et al., "Directed evolution of polymerase function by compartmentalized self-replication," Proc. Natl. Acad. Sci. USA (2001) 98: 4552-4557.
Ghadessy et al., "Generic expansion of the substrate spectrum of a DNA polymerase by directed evolution," Nat. Biotechnol. (2004) 22: 755-759.
Haase et al., "Amplification and detection of lentiviral DNA inside cells," Proc. Natl. Acad. Sci. USA (1990)87: 4971-4975.
Huang et al., "Extension of base mispairs by Taq DNA polymerase: implications for single nucleotide discrimination in PCR," Nucleic Acids Res. (1992) 20: 4567-4573.
Jestin et al., "A Method for the Selection of Catalytic Activity Using Phage Display and Proximity Coupling," Angew. Chem. Int. Ed. (1999) 38: 1124-1127.
Johnson et al., "Eukaryotic polymerases ι and ζ act sequentially to bypass DNA lesions," Nature (2000) 406: 1015-1019.
Johnson et al., "Processive DNA synthesis observed in a polymerase crystal suggests a mechanism for the prevention of frameshift mutations," Proc. Natl. Acad. Sci. USA (2003) 100: 3895-3900.
Kwok et al., "Effects of primer—template mismatches on the polymerase chain reaction: Human immunodeficiency virus type 1 model studies," Nucleic Acids Res. (1990) 18: 999-1005.
Lawyer et al., "Isolation, Characterization, and Expression in Escherichia coli of the DNA Polymerase Gene from Thermus aquaticus," J Biol. Chem. (1989) 264: 6427-6437. Li et al, "Crystal structures of open and closed forms of binary and ternary complexes of the large fragment of Thermus aquaticus DNA polymerase I: structural basis for nucleotide incorporation," EMBO J. (1998) 17: 7514-7525.
Li et al, "Structure-based design of Taq DNA polymerases with improved properties of dideoxynucleotide incorporation," Proc. Natl. Acad. Sci. USA (1999) 96: 9491-9496.
Loakes, "Survey and Summary—The applications of universal DNA base analogues," Nucleic Acids Research (2001) 29: 2437-2447.
Oberholzer, et al., "Polymerase chain reaction in liposomes," Chemistry & Biology (1995) 2: 677-682.

(Continued)

*Primary Examiner* — Kenneth R. Horlick
*Assistant Examiner* — David Thomas
(74) *Attorney, Agent, or Firm* — Edwards Wildman Palmer LLP; Elizabeth Spar; Kathleen Williams

(57) ABSTRACT

The present invention relates to the development of a novel method for the selection of nucleic acid processing and other enzymes. In particular the invention relates to a method for the selection of nucleic acid polymerases and other enzymes with desired properties based on the method of compartmentalized self-tagging.

5 Claims, 21 Drawing Sheets

OTHER PUBLICATIONS

Patel et al., "Prokaryotic DNA Polymerase I: Evolution, Structure, and "Base Flipping" Mechanism for Nucleotide Selection," J. Mol. Biol. (2001) 308: 823-837.

Patel & Loeb, "Getting a grip on how DNA polymerases function," Nature Struc. Biol (2001) 8: 656-659.

Pelletier, et al., "An in vivo library-versus-library selection of optimized protein-protein interactions," Nature Biotechnology (1999) 17: 683-690.

Schaaper, "Base Selection, Proofreading, and Mismatch Repair during DNA Replication in *Escherichia coli*," J. Biol. Chem. (1993) 268: 23762-23765.

Sepp et al., "Microbead display by in vitro compartmentalisation: selection for binding using flow cytometry," FEBS Letters (2002) 532: 455-458.

Vaisman et al., "Human DNA Polymerase ι Promiscuous Mismatch Extension," J. Biol. Chem. (2001) 276: 30615-30622.

Walde, et al., "Oparin's Reactions Revisited: Enzymatic Synthesis of Poly (adenylic acid) in Micelles and Self-Reproducing Vesicles," J. Amer. Chem. Soc. (1994) 116: 7541-7547.

Washington et al, "Human DINB1-encoded DNA polymerase κ is a promiscuous extender of mispaired primer termini," Proc. Natl. Acad. Sci. USA (2002) 99: 1910-1914.

Xia et al., "Directed evolution of novel polymerase activities: Mutation of a DNA polymerase into an efficient RNA polymerase," Proc. Natl. Acad. Sci. USA (2002) 99: 6597-6602.

Zhao et al., "Molecular evolution by staggered extension process (StEP) in vitro recombination," Nature Biotechnol. (1998) 16: 258-261.

Tawfik and Griffiths, "Man-made cell-like compartments for molecular evoluation", Nature Biotechnology, Jul. 1998, vol. 16, pp. 652-656.

PCT International Preliminary Report on Patentability, PCT/GB2004/004649, May 8, 2006 (received Jul. 13, 2006).

McGinness et al., Chem. Biol., 9(5):585-596 (2002).

Jepsen J.S. et al., Oligonucleotides, 14(2):130-146 (2004).

Christensen U.B. et al., Nucleic Acid Res., 30(22):4918-4925 (2002).

Ishihara et al., Rules for Strand Invasion by Chemically Modified Oligonucleotides Rues for Strand Invasion by Chemically Modified Oligonucleotides, JACS, 121(10):2012-2020 (1999).

Flanagan W.M., Proc. Natl. Acad. Sci. USA, 96:3513-3518 (1999).

Shchepinov M.S. et al., Nucleic Acids Research, 25(6):1155-1161 (1997).

\* cited by examiner

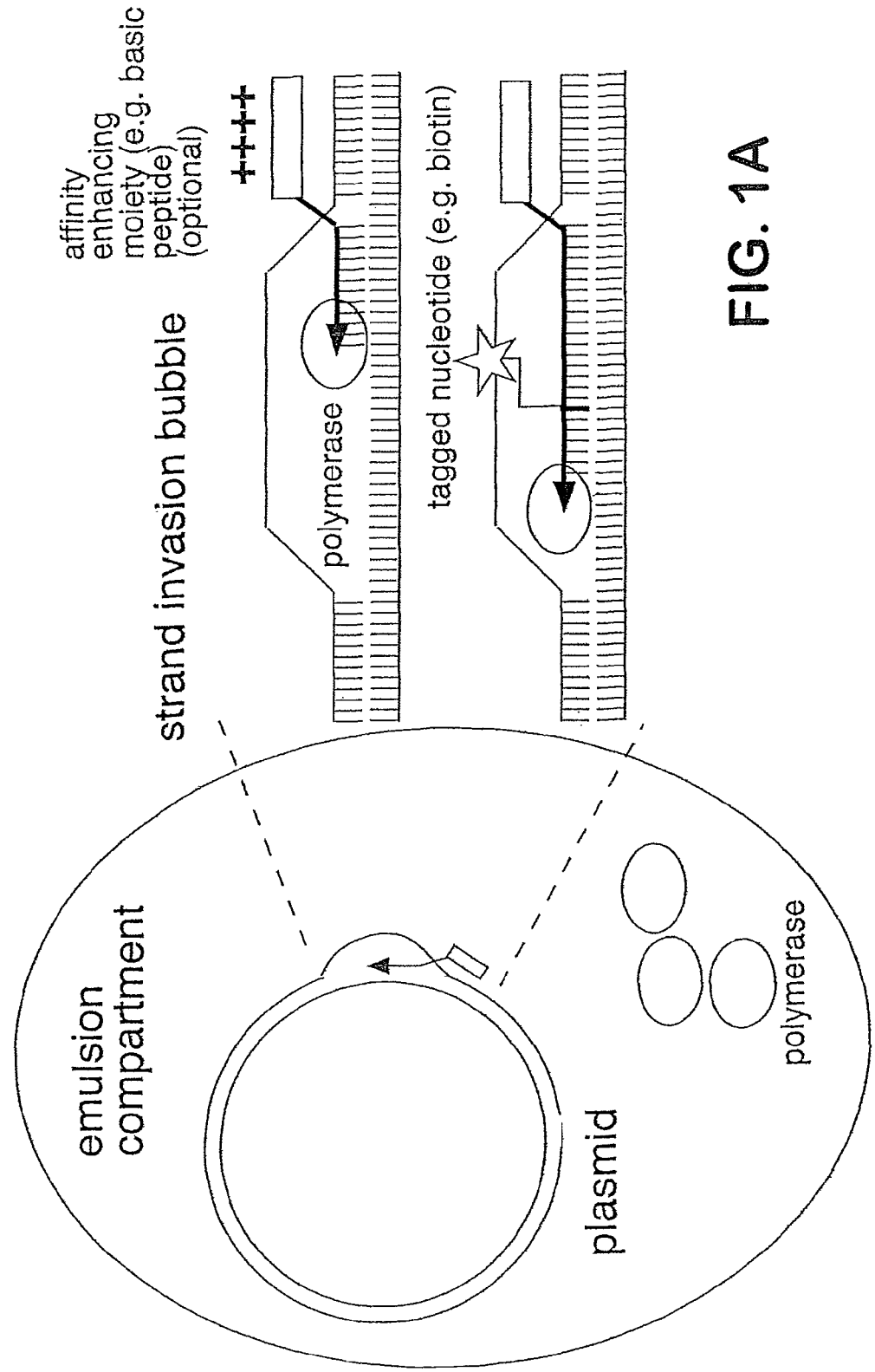

Capture

Elution

PCR or retransform

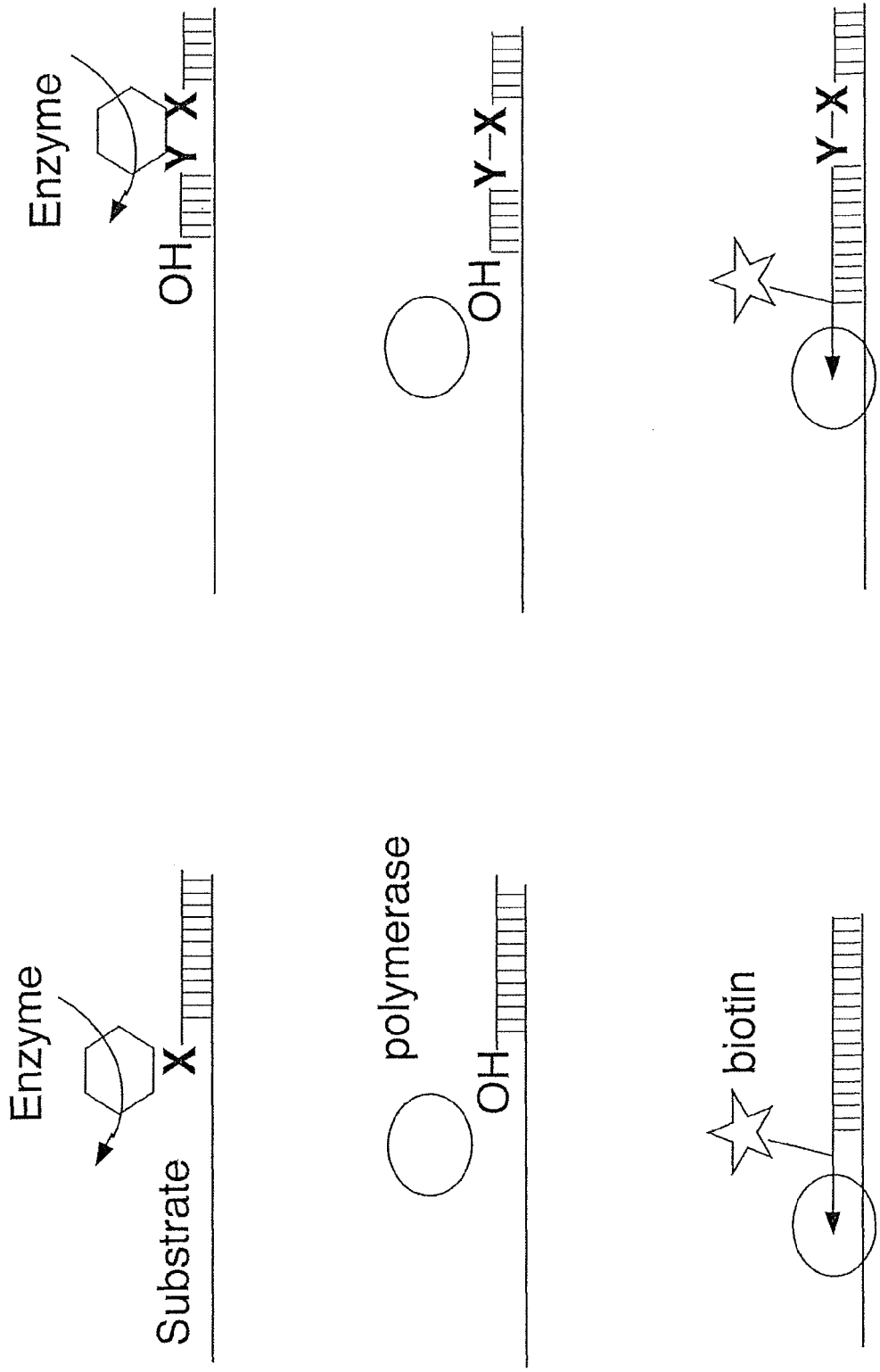

TG1 cells expressing Taq wt polymerase from pASK75

TG1 cells expressing Taq wt polymerase from pASK75 in emulsion

Efficiency of the plasmid capture with the use of 5' biotinilated primer with 108 atom linker between biotin and a base (B-108-DNA) and a 5' biotinilated primer with a 16 atom linker between biotin and a base (B-16-DNA). 108 primer 5' - Biotin - 108 atom linker - GATCTTCACCTAGATCCT-3'

```
                        SEQUENCE LISTING

<160> NUMBER OF SEQ ID NOS: 42

<210> SEQ ID NO 1
<211> LENGTH: 18
<212> TYPE: DNA
<213> ORGANISM: Artificial
<220> FEATURE:
<223> OTHER INFORMATION: Chemically synthesized

<400> SEQUENCE: 1
gatcttcacc tagatcct                                                   18

<210> SEQ ID NO 2
<211> LENGTH: 68
<212> TYPE: DNA
<213> ORGANISM: Artificial
<220> FEATURE:
<223> OTHER INFORMATION: Chemically synthesized

<400> SEQUENCE: 2
caggaaacag ctatgacaaa tctagataac gagggcaaaa aatgattgtt cttttcgttg      60
attttgac                                                              68

<210> SEQ ID NO 3
<211> LENGTH: 56
<212> TYPE: DNA
<213> ORGANISM: Artificial
<220> FEATURE:
<223> OTHER INFORMATION: Chemically synthesized

<400> SEQUENCE: 3
gtaaaacgac ggccagtcga cgcggccgct taagtatcga agaacttgtc taatcc          56

<210> SEQ ID NO 4
<211> LENGTH: 28
<212> TYPE: DNA
<213> ORGANISM: Artificial
<220> FEATURE:
<223> OTHER INFORMATION: Chemically synthesized

<400> SEQUENCE: 4
accaccgaac tgcgggtgac gccaagcg                                        28

<210> SEQ ID NO 5
<211> LENGTH: 52
<212> TYPE: DNA
<213> ORGANISM: Artificial
<220> FEATURE:
```

<223> OTHER INFORMATION: Chemically synthesized

<400> SEQUENCE: 5
gcaccaggat ccctaaggag atatacatat gagtattcaa catttccgtg tc        52

<210> SEQ ID NO 6
<211> LENGTH: 40
<212> TYPE: DNA
<213> ORGANISM: Artificial
<220> FEATURE:
<223> OTHER INFORMATION: Chemically synthesized

<400> SEQUENCE: 6
gggctcggca gtcgacttac caatgcttaa tcagtgaggc        40

<210> SEQ ID NO 7
<211> LENGTH: 75
<212> TYPE: DNA
<213> ORGANISM: Artificial
<220> FEATURE:
<223> OTHER INFORMATION: Chemically synthesized

<400> SEQUENCE: 7
ggcgactcta gataacgagg gcaaaaaatg cgtggtatgc ttcctctttt tgagcccaag        60
ggccgcgtcc tcctg        75

<210> SEQ ID NO 8
<211> LENGTH: 40
<212> TYPE: DNA
<213> ORGANISM: Artificial
<220> FEATURE:
<223> OTHER INFORMATION: Chemically synthesized

<400> SEQUENCE: 8
gcggtgcgga gtcgactcac tccttggcgg agagccagtc        40

<210> SEQ ID NO 9
<211> LENGTH: 21
<212> TYPE: DNA
<213> ORGANISM: Artificial
<220> FEATURE:
<223> OTHER INFORMATION: Chemically synthesized
<220> FEATURE:
<221> NAME/KEY: misc_feature
<222> LOCATION: (4)..(4)
<223> OTHER INFORMATION: n is G-clamp, cytosine analog

<400> SEQUENCE: 9
aagnatcttc acctagatcc t        21

<210> SEQ ID NO 10
<211> LENGTH: 21
<212> TYPE: DNA
<213> ORGANISM: Artificial
<220> FEATURE:
<223> OTHER INFORMATION: Chemically synthesized
<220> FEATURE:
<221> NAME/KEY: misc_feature
<222> LOCATION: (4)..(4)
<223> OTHER INFORMATION: n is a G clamp, cytosine analog

<400> SEQUENCE: 10
aagnatcttc acctagatcc t        21

<210> SEQ ID NO 11
<211> LENGTH: 25
<212> TYPE: DNA

```
<213> ORGANISM: Artificial
<220> FEATURE:
<223> OTHER INFORMATION: Chemically synthesized
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (9)..(9)
<223> OTHER INFORMATION: n is 2,6-diaminopurine

<400> SEQUENCE: 11
cnananggnt cttcacctag atcct                                      25

<210> SEQ ID NO 12
<211> LENGTH: 25
<212> TYPE: DNA
<213> ORGANISM: Artificial
<220> FEATURE:
<223> OTHER INFORMATION: Chemically synthesized
<220> FEATURE:
<221> NAME/KEY: misc_feature
<222> LOCATION: (2)..(2)
<223> OTHER INFORMATION: n is 2, 6 diaminopurine
<220> FEATURE:
<221> NAME/KEY: misc_feature
<222> LOCATION: (4)..(4)
<223> OTHER INFORMATION: n is 2, 6 diaminopurine
<220> FEATURE:
<221> NAME/KEY: misc_feature
<222> LOCATION: (6)..(6)
<223> OTHER INFORMATION: n is 2, 6 diaminopurine
<220> FEATURE:
<221> NAME/KEY: misc_feature
<222> LOCATION: (9)..(9)
<223> OTHER INFORMATION: n is 2, 6 diaminopurine

<400> SEQUENCE: 12
cnananggnt cttcacctag atcct                                      25

<210> SEQ ID NO 13
<211> LENGTH: 39
<212> TYPE: DNA
<213> ORGANISM: Artificial
<220> FEATURE:
<223> OTHER INFORMATION: Chemically synthesized
<220> FEATURE:
<221> NAME/KEY: misc_feature
<222> LOCATION: (5)..(5)
<223> OTHER INFORMATION: n is 2, 6 diaminopurine
<220> FEATURE:
<221> NAME/KEY: misc_feature
<222> LOCATION: (8)..(8)
<223> OTHER INFORMATION: n is 2, 6 diaminopurine
<220> FEATURE:
<221> NAME/KEY: misc_feature
<222> LOCATION: (10)..(10)
<223> OTHER INFORMATION: n is 2, 6 diaminopurine
<220> FEATURE:
<221> NAME/KEY: misc_feature
<222> LOCATION: (13)..(13)
<223> OTHER INFORMATION: n is 2, 6 diaminopurine
<220> FEATURE:
<221> NAME/KEY: misc_feature
<222> LOCATION: (16)..(16)
<223> OTHER INFORMATION: n is 2, 6 diaminopurine
```

```
<400> SEQUENCE: 13
ggtcntgngn ttntcnaaaa ggatcttcac ctagatcct                     39

<210> SEQ ID NO 14
<211> LENGTH: 25
<212> TYPE: DNA
<213> ORGANISM: Artificial
<220> FEATURE:
<223> OTHER INFORMATION: Chemically synthesized

<400> SEQUENCE: 14
caaaaaggat cttcacctag atcct                                    25

<210> SEQ ID NO 15
<211> LENGTH: 20
<212> TYPE: DNA
<213> ORGANISM: Artificial
<220> FEATURE:
<223> OTHER INFORMATION: Chemically synthesized

<400> SEQUENCE: 15
aagccatacc aaacgacgag                                          20

<210> SEQ ID NO 16
<211> LENGTH: 20
<212> TYPE: DNA
<213> ORGANISM: Artificial
<220> FEATURE:
<223> OTHER INFORMATION: Chemically synthesized

<400> SEQUENCE: 16
ttgccgggaa gctagagtaa                                          20

<210> SEQ ID NO 17
<211> LENGTH: 18
<212> TYPE: DNA
<213> ORGANISM: Artificial
<220> FEATURE:
<223> OTHER INFORMATION: Chemically synthesized

<400> SEQUENCE: 17
gatcttcacc tagatcct                                            18

<210> SEQ ID NO 18
<211> LENGTH: 19
<212> TYPE: DNA
<213> ORGANISM: Artificial
<220> FEATURE:
<223> OTHER INFORMATION: Chemically synthesized

<400> SEQUENCE: 18
catgccatcc gtaagatgc                                           19

<210> SEQ ID NO 19
<211> LENGTH: 19
<212> TYPE: DNA
<213> ORGANISM: Artificial
<220> FEATURE:
<223> OTHER INFORMATION: Chemically synthesized

<400> SEQUENCE: 19
gttcctggcc ttttgctgg                                           19

<210> SEQ ID NO 20
<211> LENGTH: 16
<212> TYPE: DNA
```

```
<213> ORGANISM: Artificial
<220> FEATURE:
<223> OTHER INFORMATION: Chemically synthesized

<400> SEQUENCE: 20
acgtagtggg ccatcg                                                    16

<210> SEQ ID NO 21
<211> LENGTH: 18
<212> TYPE: DNA
<213> ORGANISM: Artificial
<220> FEATURE:
<223> OTHER INFORMATION: Chemically synthesized

<400> SEQUENCE: 21
gatcttcacc tagatcct                                                  18

<210> SEQ ID NO 22
<211> LENGTH: 18
<212> TYPE: DNA
<213> ORGANISM: Artificial
<220> FEATURE:
<223> OTHER INFORMATION: Chemically synthesized

<400> SEQUENCE: 22
gatcttcacc tagatcct                                                  18

<210> SEQ ID NO 23
<211> LENGTH: 18
<212> TYPE: DNA
<213> ORGANISM: Artificial
<220> FEATURE:
<223> OTHER INFORMATION: Chemically synthesized

<400> SEQUENCE: 23
gatcttcacc tagatcct                                                  18

<210> SEQ ID NO 24
<211> LENGTH: 18
<212> TYPE: DNA
<213> ORGANISM: Artificial
<220> FEATURE:
<223> OTHER INFORMATION: Chemically synthesized

<400> SEQUENCE: 24
gatcttcacc tagatcct                                                  18

<210> SEQ ID NO 25
<211> LENGTH: 14
<212> TYPE: DNA
<213> ORGANISM: Artificial
<220> FEATURE:
<223> OTHER INFORMATION: Chemically synthesized

<400> SEQUENCE: 25
ttcacctaga tcct                                                      14

<210> SEQ ID NO 26
<211> LENGTH: 12
<212> TYPE: DNA
<213> ORGANISM: Artificial
<220> FEATURE:
<223> OTHER INFORMATION: Chemically synthesized

<400> SEQUENCE: 26
cacctagatc ct                                                        12
```

```
<210> SEQ ID NO 27
<211> LENGTH: 10
<212> TYPE: DNA
<213> ORGANISM: Artificial
<220> FEATURE:
<223> OTHER INFORMATION: Chemically synthesized

<400> SEQUENCE: 27
cctagatcct                                                              10

<210> SEQ ID NO 28
<211> LENGTH: 8
<212> TYPE: DNA
<213> ORGANISM: Artificial
<220> FEATURE:
<223> OTHER INFORMATION: Chemically synthesized

<400> SEQUENCE: 28 tagatcct                                                                8

<210> SEQ ID NO 29
<211> LENGTH: 18
<212> TYPE: DNA
<213> ORGANISM: Artificial
<220> FEATURE:
<223> OTHER INFORMATION: Chemically synthesized

<400> SEQUENCE: 29
gatcttcacc tagatcct                                                     18

<210> SEQ ID NO 30
<211> LENGTH: 15
<212> TYPE: DNA
<213> ORGANISM: Artificial
<220> FEATURE:
<223> OTHER INFORMATION: Chemically synthesized

<400> SEQUENCE: 30
aaatttgatc acttc                                                        15

<210> SEQ ID NO 31
<211> LENGTH: 15
<212> TYPE: DNA
<213> ORGANISM: Artificial
<220> FEATURE:
<223> OTHER INFORMATION: Chemically synthesized

<400> SEQUENCE: 31
aaatttgatc acttc                                                        15

<210> SEQ ID NO 32
<211> LENGTH: 15
<212> TYPE: DNA
<213> ORGANISM: Artificial
<220> FEATURE:
<223> OTHER INFORMATION: Chemically synthesized

<400> SEQUENCE: 32
aaatttgatc acttc                                                        15

<210> SEQ ID NO 33
<211> LENGTH: 18
<212> TYPE: DNA
<213> ORGANISM: Artificial
<220> FEATURE:
<223> OTHER INFORMATION: Chemically synthesized
```

```
<400> SEQUENCE: 33
gatcttcacc tagatcct                                                  18

<210> SEQ ID NO 34
<211> LENGTH: 19
<212> TYPE: DNA
<213> ORGANISM: Artificial
<220> FEATURE:
<223> OTHER INFORMATION: Chemically synthesized

<400> SEQUENCE: 34
catgccatcc gtaagatgc                                                 19

<210> SEQ ID NO 35
<211> LENGTH: 19
<212> TYPE: DNA
<213> ORGANISM: Artificial
<220> FEATURE:
<223> OTHER INFORMATION: Chemcially synthesized

<400> SEQUENCE: 35
gttcctggcc ttttgctgg                                                 19

<210> SEQ ID NO 36
<211> LENGTH: 16
<212> TYPE: DNA
<213> ORGANISM: Artificial
<220> FEATURE:
<223> OTHER INFORMATION: Chemically synthesized

<400> SEQUENCE: 36
acgtagtggg ccatcg                                                    16

<210> SEQ ID NO 37
<211> LENGTH: 18
<212> TYPE: DNA
<213> ORGANISM: Artificial
<220> FEATURE:
<223> OTHER INFORMATION: Chemically synthesized

<400> SEQUENCE: 37
gatcttcacc tagatcct                                                  18

<210> SEQ ID NO 38
<211> LENGTH: 14
<212> TYPE: DNA
<213> ORGANISM: Artificial
<220> FEATURE:
<223> OTHER INFORMATION: Chemically synthesized

<400> SEQUENCE: 38
ttcacctaga tcct                                                      14

<210> SEQ ID NO 39
<211> LENGTH: 12
<212> TYPE: DNA
<213> ORGANISM: Artificial
<220> FEATURE:
<223> OTHER INFORMATION: Chemcially synthesized

<400> SEQUENCE: 39
cacctagatc ct                                                        12

<210> SEQ ID NO 40
<211> LENGTH: 10
<212> TYPE: DNA
```

```
<213> ORGANISM: Artificial
<220> FEATURE:
<223> OTHER INFORMATION: Chemically synthesized

<400> SEQUENCE: 40
cctagatcct                                                            10

<210> SEQ ID NO 41
<211> LENGTH: 8
<212> TYPE: DNA
<213> ORGANISM: Artificial
<220> FEATURE:
<223> OTHER INFORMATION: Chemically synthesized

<400> SEQUENCE: 41 tagatcct                                                               8

<210> SEQ ID NO 42
<211> LENGTH: 6
<212> TYPE: DNA
<213> ORGANISM: Artificial
<220> FEATURE:
<223> OTHER INFORMATION: Chemically synthesized

<400> SEQUENCE: 42 caaaaa                                                                 6
```

COMPARTMENTALIZED SELF TAGGING

RELATED APPLICATIONS

This application is a continuation of Application U.S. Ser. No. 11/417,449, which was filed on 3 May 2006, now U.S. Pat. No. 7,691,576, which is a continuation of Application No. PCT/GB04/004649, which was filed on 3 Nov. 2004, which designated the United States and was published in English, and which claims the benefit of United Kingdom Application GB0325653.4 filed 3 Nov. 2003. The entire teachings of the above applications are incorporated herein by reference.

FIELD OF THE INVENTION

The present invention relates to the development of a novel method for the selection of nucleic acid processing and other enzymes. In particular the invention relates to a method for the selection of nucleic acid polymerases and other enzymes with desired properties based on the method of compartmentalized self-tagging.

BACKGROUND

Compartmentalization methods based on water-in-oil emulsions have recently been developed for the use in repertoire selection methods (Griffiths98/Ghadessy 01/Sepp02/Griffiths). Compartmentalization segregates individual genes and their encoded products (delivered either as cells (Ghadessy) or expressed in situ (Griffiths/Sepp)) into discrete, physically separate aqueous compartments, thus ensuring the linkage of genotype and phenotype during the selection process. After selection, genes encoding the desired enzymatic activities are isolated either through modification (e.g. methylation), by display on beads (Sepp/Griffiths) or by amplification (Ghadessy 01).

Amplification (CSR) and bead capture (IVC) have been exemplified for the selection of novel enzymatic activities, i.e. variants of Taq polymerase that are either more theiinostable or resistant to the inhibitor heparin (Ghadessy 01) or variants of phosphotriesterase (Griffiths 03) that show increased turn-over. However, both methods depend on high catalytic turn-over (and/or processivity in the case of polymerases) and appear to be poorly suited for the selection of enzymes with a low turnover. While strong selective pressure for a high enzymatic turnover is desirable as an end-point it limits the type of catalytic activities that can be accessed using the system. In particular, starting even from a highly active enzyme, substantial modifications of substrate specificity or even catalytic mechanism are likely to result in much reduced catalytic turn-over, because high-activity enzymes may be many mutations away from the starting sequence and may therefore not be accessible within the limits of the molecular repertoires that can be handled realistically by CSR (or IVC) ($10^{10}$). For example: From kinetic studies of $E. coli$ DNA polymerase I, mutations such as E710A increased affinity and incorporation of ribonucleotides at the expense of lower catalytic rates and less affinity for wild-type substrates (deoxyribonucleotides) (1). The corresponding mutant of Taq DNA polymerase I, E615A, could incorporate ribonucleotides more efficiently than wild-type polymerase. However, it was only able to synthesize very short fragments and not the full-length Taq gene (J. L. Ong, P. H. unpublished results). In another selection experiment in which Beta-glucuronidase was evolved into a Beta-galactosidase, the desired phenotype was obtained after several rounds of selection but at the expense of catalytic activity. It was also found that selected variants in the initial rounds of selection were able to catalyze the conversion of several different substrates not utilized by either parental enzyme, and at much lower catalytic rates (2). Thus, for many selection objectives (e.g. altered substrate specificity) it is likely that intermediates along the evolutionary trajectory to the new phenotype will have reduced catalytic activity. It would therefore be desirable to have a method for selection of polymerase (and other enzymatic) activities with a lower threshold of selection (ideally requiring just a single turnover event).

For the selection of polymerases with lower catalytic activity or processivity, the present inventors had previously proposed a modification of CSR called short-patch CSR (spCSR) in which only, a small region (a "patch") of the gene under investigation is randomized and replicated (see original CSR patent). spCSR has allowed the selection of variants of Taq polymerase capable of utilizing ribonucleotide instead of deoxiribonucleotide triphosphates as substrates, which could not be isolated using standard CSR. However, spCSR still requires hundreds to thousands of turnover events for the enzyme to become selectable.

Theoretically, the method of CSR using biotin labelled nucleotides (described in general in PCT/GB98/01889) might be used to detect single turnover events of enzymes, for example polymerases. However in practice the present inventors have found that this method is not optimally efficient for several reasons:

In situ expression of polymerases (inside compartments) from a linear DNA fragment comprising polymerase gene and for example a T7 promotor can be achieved using an in vitro transcription/translation system (ivt) (such as are commercially available). However, we have found that the presence of biotinylated nucleotides (Biotin-dNTP) results in tagging of the 3' ends of the linear fragment with Biotin regardless of the activity of the expressed polymerase and regardless of the nature of the 3' end (5' overhang, blunt, or 3' overhang). This results in such high-level background that a single-turnover event of a polymerase of interest is not detectable above it.

The present inventors consider that the reasons for this are: that some ivt extracts themselves contain endogenous terminal transferase (TT) activity, T7 RNA pol itself has substantial TT activity (see e.g. McGinness et al (2002) Chem. Biol., 9, 585-596) and is present even before any polymerase of interest has been expressed and so has a head-start in modifying free 3' ends DNA polymerases (as far as tested by the present inventors) are poorly expressed by ivt systems, DNA polymerases are poorly active in the ivt buffers (as far as tested by the present inventors).

Possible technical solutions to this include the following:
1) conditionally blocked 3' ends. The problem with this approach is that the chemistry is challenging. In addition, this method does not solve the problem of the polymerases being poorly expressed by ivt systems and being poorly active in ivt buffers.
2) The 2-step method described in PCT/GB01/04108 in the name of the present inventors: 2-step ivt followed by testing for the resultant polymerase to extend DNA. The disadvantage with this method is that it is time-consuming to perform. In addition, it does not solve the problem that DNA polymerases are poorly expressed by ivt systems.

Other methods for the selection of polymerases, include the method of "proximity coupling" used in phage display.

Such a method involves the proximal display of both substrate and enzyme on the phage particle (Neri 99, Schultz 00). This concept relies on the in cis conversion of substrate to product or in the case of polymerases the incorporation of a tagged nucleotide into a template-primer duplex substrate tethered to the phage particle (Jestin01, Xia 02). Recently, the method has been used successfully to select for a variant of the Taq polymerase Stoffel fragment that incorporates ribonucleoside triphosphates (rNTPs) with efficiencies approaching those of the wild-type enzyme for dNTP substrates (Xia 02). However, there are several problems associated with the use of this method. Importantly, selection conditions have to be compatible with phage viability and the intramolecular tethering of the substrate may favor the selection of polymerases with low affinity for template-primer duplex and poor processivity.

Therefore, there remains a need in the art for the provision of a method for the selection of nucleic acid processing molecules, in particular DNA polymerases which possess a low catalytic turnover and/or processivity, which method is not constrained by selection conditions which are required for phage viability.

SUMMARY OF THE INVENTION

The present inventors have previously devised a method for the selection of nucleic acid processing enzymes, which possess a desired activity. Such method is known as directed evolution and such method uses the technique of compartmentalised self replication (CSR). Both procedures are described in PCT/01/04108 and GB/002/005216.

The present inventors have now devised an alternative method based on the technique of 'compartmentalised self replication' (CSR) for the selection of nucleic acid processing enzymes, particularly polymerases which may be particularly suited for the isolation of enzymes with lower catalytic turnover. The method is called CST (compartmentalized self-tagging). It is based on capture of a plasmid encoding the polymerase or other binding agent by virtue of activity dependent tagging with an oligonucleotide.

Such a method has several advantages over the prior art methods used for the selection of nucleic acid processing enzymes. That is, it unites the respective advantages of CSR and proximity coupling:

It does not select for those enzymes which have a low affinity for substrate (primer-template duplex) and which therefore may have limited practical uses, and The selection conditions of the method are not restricted to those which are required for phage viability, thus allowing a much greater range of enzymes to be selected for then those prior art methods which rely on the technique of phage display.

at the same time it is not dependent on the complete replication of the polymerase encoding gene. In fact, priming may occur anywhere on the plasmid or linear DNA fragment encoding the polymerase and selection may require the incorporation of but few nucleotides.

CST unlike CSR is suitable for the selection of polymerases with a high-error rate (if arbitrarly a high-error rate is defined as approximately 1/N errors per replication cyle for a polymerase gene of N bases). For such polymerases CSR leads to an accumulation of deleterious mutations during self-replication. As a result a large proportion of the "offspring" genes will encode polymerase with compromised activity due to the mutations. This effect is particularly pronounced for polymerases that make a large number of frame-shifting errors as the majority of these can be expected to completely destroy activity in the affected clones. In contrast in CST, it is the parent plasmid, which provides, i.e. encodes the gene sequence of the selected polymerase. The actual primer extension product only serves as a "tag" by which the parent plasmid is isolated. Therefore any errors incorporated during primer extension do not transfer to the "offspring".

CST is superior to CSR for the evolution and selection of polymerases incorporating modified nucleotide or other substrates, in cases where those modifications preclude replication of the extension products by available polymerases. In other words, amplification of the offspring genes from CSR would be impossible because these would contain replication blocking modifications to the DNA chemistry. In contrast in CST, the selection products need not be "reamplifiable". It is the parent plasmid, which provides the gene sequence of the selected polymerase. The actual primer extension product only serves as a "tag" by which the parent plasmid is isolated. Therefore any blocking modified nucleotides or other substrates incorporated during primer extension do not prevent recovery and re-amplification of the "offspring" genes. In fact, the extension products need not be chemically close or even related to nucleic acids.

Thus in a first aspect the present invention provides a method for the selection of an enzyme capable of directly or indirectly modifying an oligonucleotide wherein the method is not dependent on the complete replication of the oligonucleotide modifying enzyme encoding gene, which method comprises the steps of:

(a) Providing one or more nucleic acid molecules in the faun of parent plasmids encoding one or more enzymes of interest, wherein the parent plasmid provides the gene sequence of the selected enzyme of interest.

(b) Compartmentalising those plasmids according to step (a), such that each compartment comprises a plasmid together with the one or more enzymes encoded by the plasmid and an oligonucleotide specific for a region on the plasmid according to step (a).

(c) Providing conditions such that stable association of the oligonucleotide according to step (b) with a region of the plasmid is capable of occurring;

(d) Providing conditions such that modification of the oligonucleotide according to step (b) using the enzyme encoded by the plasmid is capable of occurring and such that the resultant modified oligonucleotide comprises a molecular tag; and (e) Capturing the modified oligonucleotide/plasmid complex.

According to the methods described herein, preferably the 'one or more nucleic acid molecules' according to step (a) is a plurality of nucleic molecules.

Advantageously, the method of the invention may be used for the selection of enzymes comprising one or more of the following properties: low catalytic turnover (under the selection conditions), low processivity (under the selection conditions), polymerases which incorporate modified replication-blocking nucleotide or other substrates that cannot be replicated and polymerases with a high-error rate (approximately >1/N errors for a polymerase gene of N bases).

According to the method described herein the term 'an oligonucleotide' refers to any sequence of single stranded nucleic acid. An oligonucleotide may be a partially or wholly artificial single stranded nucleic acid molecule consisting of exclusively synthetic or a mixture of naturally-occurring and synthetic bases, any one of the foregoing linked to a polypeptide, and any one of the foregoing linked to any other molecular group or construct. Advantageously, the other molecular group or construct may be selected from the group consisting of nucleic acids, polymeric substances, particularly beads, for example polystyrene beads, magnetic substances such as magnetic beads, labels, such as fluorophores or isotopic labels, chemical reagents, binding agents such as macrocycles and the like. According to the invention described herein, an oligonucleotide for use according to the method is capable of specific hybridisation with a region on a plasmid according to the method of the invention, either prior to modification of the oligonucleotide or subsequent to modification of the oligonucleotide. Advantageously, an oligonucleotide for use according to the method of the invention is capable of specific hybridisation with a region on a plasmid according to the method of the invention prior to modification of the oligonucleotide. According to the method of the present invention, one skilled in the art will appreciate that any oligonucleotide suitable for use according to the method of the invention for polymerases must also be "extendable", e.g. have either from the start or after suitable processing a free and accessible 3' end.

As referred to herein the term 'modification of an oligonucleotide' refers to an alteration in the structure of the oligonucleotide. Such alterations include but are not limited to any one or more of the group consisting of the following: extension of the oligo (either 5' or 3'); ligation of an oligonucleotide to another entity, in particular a further oligonucleotide; phosphorylation of the oligonucleotide followed by tag ligation as herein described, conversion of a entity linked to the oligonucleotide to a different entity, for example conversion of a substrate linked to the oligonucleotide to a product; attachment of a molecular group to the oligonucleotide, for example H2O2, HRP biotin tyramide; the modification of antenna molecules/scavenger molecules linked to the oligonucleotide.

According to the method herein described, modification of the oligonucleotide may be direct or indirect. However, in either case, it is an essential feature of the invention that the result of oligonucleotide modification is that a molecular tag/capture tag is generated on the oligonucleotide for example by incorporation. This molecular tag/capture tag allows the subsequent capture of the plasmid/oligonucleotide complex.

Suitable 'molecular tags/capture tags' are described in the detailed description of the invention. Those skilled in the art will appreciate that the details of the method of generation of molecular tags on an oligonucleotide according to the invention will depend upon the properties of the enzyme of interest.

In the case that the enzyme of interest is a DNA polymerase then incorporation of one or more tagged nucleotides into the 3' end of the DNA sequence is used to generate a capture tag/molecular tag as part of the oligonucleotide using the DNA polymerase. Furthermore, in the case that the enzyme of interest is a ligase, then the molecular tag is incorporated into the oligonucleotide via the ligation of a second tagged oligonucleotide to the oligonucleotide which is associated with the plasmid according to the invention. Furthermore, in the case that the enzyme of interest is a polynucleotide kinase, then incorporation of a molecular tag occurs via the 5' phoshorylation and ligation of a second oligonucleotide, which bears a molecular tag. Those skilled in the art will appreciate that this list is not intended to be exhaustive.

According to the method of the invention, enzymes which are particularly suitable for selection using the method of the present invention are those which cannot be successfully selected using the method of CSR. As described earlier these include but are not limited to enzymes with any one or more of the following properties: low catalytic turnover, low substrate processivity, polymerases which incorporate modified nucleotide substrates and polymerases with a high-error rate (approximately 1/N errors for a polymerase gene of N bases).

The present inventors have found that these enzymes are difficult to select by CSR because they struggle to self-replicate under the selection conditions and/or (for example in the case of S. solfataricus Dpo4) they are so error-prone that upon self-replication they corrupt their own coding information. Therefore, the method of the invention extends the range of polymerases that can be selected over and above those available for selection using CSR.

Thus, suitable enzymes for selection using the method of the invention include any one or more of those selected from the group consisting of the following: nucleic acid processing enzymes, enzymes which act on one or more substrates of nucleic acid replicases (that is, enzymes indirectly involved in nucleic acid processing), enzymes which modulate the activity of replicase inhibitors (that is, enzymes indirectly involved in nucleic acid processing), enzymes which act directly on a substrate molecule linked to an oligonucleotide wherein the oligonucleotide is capable of stable association with a region of a plasmid encoding that enzyme according to the method of the invention, or enzymes which act indirectly on a substrate molecule linked to an oligonucleotide, wherein the oligonucleotide is capable of stable association with a region of a plasmid encoding that enzyme according to the method of the invention.

Accordingly those skilled in the art will appreciate that the term (modification of the oligonucleotide) 'using the enzyme encoded by the plasmid is capable of occurring' includes within its scope the direct use of an enzyme encoded by the plasmid to generate a molecular tag in the oligonucleotide (for example by the incorporation of tagged nucleotides into an oligonucleotide in the case where the enzyme is a nucleic acid replicase). In addition the term '(modification of the oligonucleotide) 'using the enzyme encoded by the plasmid is capable of occurring' includes within its scope the indirect use of an enzyme of interest to tag the oligonucleotide associated with the plasmid according to the method of the invention. Such indirect use would be for example, the conversion of a substrate linked to an oligonucleotide to a product in the presence of an enzyme encoded by the plasmid. In this case the 'molecular tag/capture tag' as herein defined is the product.

Any plasmid is suitable for use according to the method of the invention. Suitable plasmids are given in the detailed description of the invention.

According to the method of the invention, the term 'stable association' (of an oligonucleotide specific for a region on the plasmid with the plasmid) refers to the stable hybridisation of an oligonucleotide with the plasmid such that a plasmid encoding the enzyme of interest may be captured using the molecular tag present on the oligonucleotide.

Suitable methods for capturing the modified oligonucleotide/plasmid complex include the selection using a molecular tag/capture tag binding agent attached to a solid support. Such binding agents include but are not limited to antibodies specific for the molecular tag. In the case that the molecular tag is biotin then a suitable molecular tag binding agent is strepavidin. Those skilled in the art will be aware of other suitable molecular tag/capture tags and molecular tag/capture tag binding agents.

In a preferred embodiment of the above aspect of the invention the method is for the selection of nucleic acid processing enzymes which method is not dependent on the complete replication of the nucleic acid processing enzyme encoding gene, which method comprises the steps of:

(a) Providing one or more nucleic acid molecules in the foam of parent plasmids encoding one or more nucleic acid processing enzymes of interest, wherein the parent plasmid provides the gene sequence of the selected nucleic processing enzyme of interest.
(b) Compartmentalising those plasmids according to step (a), such that each compartment comprises a plasmid together with the one or more nucleic acid processing enzymes encoded by the plasmid
(c) Providing conditions such that stable association of an oligonucleotide specific for a region on the plasmid according to step (b) with that region of the plasmid is capable of occurring;
(d) Providing conditions such that extension of the oligonucleotide according to step (c) using the nucleic acid processing enzyme in the presence of one or more modified nucleotides comprising a molecular tag is capable of occurring; and
(e) Capturing the modified oligonucleotide/plasmid complex.

Suitable nucleic acid processing enzymes for use according to the method of the invention include any of those selected from the group consisting of the following: replicases, in particular DNA replicases; DNA ligases, RNA ligases, polynucleotide kinases, enzymes which are indirectly involved in nucleic acid processing.

Suitable DNA replicases include any of DNA replicases from families polA, polB, polC, polD, polY & polX or RT. The method may be particularly suited for members of these families, which have lower processivity or activity (under the selection conditions), which makes them difficult to select by CSR.

In the case that the method of the invention is for the selection of DNA polymerases which possess a low processivity and/or catalytic turnover the method comprises the following steps:
(a) Providing one or more nucleic acids molecules in the form of plasmids encoding one or more DNA polymerases,
(b) Compartmentalising those plasmids according to step (a), such that each compartment comprises a plasmid together with the one or more DNA polymerases encoded by the plasmid; and an oligonucleotide specific for a region on the plasmid according to step (a) with that region of the plasmid
(c) Providing conditions such that stable association of the oligonucleotide specific for a region on the plasmid according to step (a) with that region of the plasmid is capable of occurring;
(d) Providing conditions such that the 3' end of the oligonucleotide according to step (b) is capable of being extended using the DNA polymerase according to step (a) in the presence of one or more modified nucleotides comprising a molecular tag; and
(e) Capturing the 3' extended modified oligonucleotide/plasmid complex.

In the case of the selection of polymerase activity, in its simplest form CST involves three steps:
1) hybridization: an oligonucleotide specific for a region on a plasmid is hybridized to the plasmid (for example by melting or strand-invasion of a defined region of DNA and annealing to one of the strands) and thus becomes stably associated with it (FIG. 1)
2) tagging: the oligonucleotide is modified (for example 3' extended) by the polymerase of interest encoded by the plasmid and expressed from it. Modification entails for example extension of the 3' end of the oligonucleotide by the polymerase in the presence of modified nucleotides bearing a molecular tag (for example biotin) (FIG. 1)
3) capture: Incorporation of the tagged nucleotides subsequently allows capture of the plasmids encoding an active polymerase, for example on streptavidin coated beads in the case where the molecular tag is biotin. (FIG. 1B) Plasmids encoding inactive polymerases do not have their associated oligonucleotides extended and therefore will not be captured and be lost from the gene pool. Captured plasmids can be eluted from the beads and directly retransformed. Alternatively, the polymerase gene may be PCR amplified directly from the beads and recloned, as shown in FIG. 1B. Details will be given in the detailed description of the invention.

The method of the present invention may be particularly suitable for the selection of DNA polymerases which are naturally distributive or poorly processive, such as members of the polY or polX family or low-processivity variants of high processivity polymerases such as the Stoffel fragment of Taq polymerase or T7 DNA polymerase in the absence of thioredoxin. Alternatively, starting from a highly active and processive polymerase CST may allow evolutionary trajectories that are populated with variants of greatly reduced turn-over and/or processivity, such as are likely to be encountered when making changes to substrate or extension chemistry.

According to the method of the invention, the term 'substrate processivity/processivity' means the number of nucleotides incorporated during a single cycle of binding primer-template duplex and extension before dissociation.

As referred to herein, the term 'catalytic turnover/turnover' means the number of nucleotides incorporated into product in a certain amount of time. At low enzyme and or template concentrations processivity is important as binding of the template-primer duplex substrate becomes a rate-limiting step. In contrast, at high enzyme and/or template concentrations low processivity can at least partially be compensated by fast rebinding of enzyme to primer-template duplex.

According to an alternative embodiment of the invention, the method is for the selection of polynucleotide kinases. In this embodiment of the invention, the oligonucleotide is extended in the presence of the polynucleotide kinase via phosphorylation of the 5' end of the oligonucleotide followed by the incorporation of a one or more tagged nucleotides at the 5' end of the oligonucleotide (tag ligation). In this embodiment of the invention, each compartment comprises the plasmid encoding the polynucleotide kinase, the kinase itself, one or more oligonucleotides which are capable of stable association with the plasmid. In addition the compartment also comprises a ligase which is required for the extention of the 5' phosphorylated oligonucleotide.

In a further preferred embodiment of the above aspect of the invention the method is for the selection of nucleic acid ligases. Suitable ligases for selection include DNA and RNA ligases. According to this aspect of the invention each compartment comprises one or more oligonucleotides capable of association with a plasmid encoding the ligase, a plasmid encoding the ligase of interest, the ligase encoded by the plasmid and one or more tagged nucleotides in the form of tagged oligonucleotides for ligation to the oligonucleotide. Advantageously, according to this embodiment of the invention, an untagged oligonucleotide which is stably associated with the plasmid encoding it will become tagged via the ligation of a tagged oligonucleotide to the untagged oligonucleotide 3' end. In this way selection of the oligonucleotide/ligase/plasmid complex is achieved.

Alternatively, the selection of a ligase using the method of the invention may involve the 3' ligation of two or more oligos (at least one of which bears a molecular tag) which in isolation are incapable of stable association with a plasmid encoding the ligase. However, once ligated, the resultant tagged oligonucleotide is capable of stable association with the plasmid encoding the ligase and thus the ligase/oligonucleotide/plasmid complex may be selected via the molecular tag.

Thus in a further preferred embodiment of the method of the invention there is provided a method for the selection of an oligonucleotide ligase wherein the method is not dependent on the complete replication of the oligonucleotide ligase enzyme encoding gene
(a) Providing one or more nucleic acids molecules in the foim of parent plasmid/s encoding one or more oligonucleotide ligases, wherein the parent plasmid/s provides the gene sequence of the selected ligase of interest.
(b) Compartmentalising those plasmids according to step (a), such that each compartment comprises a plasmid together with the one or more ligases encoded by the plasmid, two or more oligonucleotides which are specific for a region on the plasmid at least one of which bears a molecular tag, wherein each oligonucleotide in isolation is not capable of stable association with the plasmid on ligation is capable of stable association with the plasmid.
(c) Stably associating an oligonucleotide specific for a region on the plasmid according to step (a) with that region of the plasmid;
(d) Extending the oligonucleotide according to step (a) using the nucleic acid processing enzyme in the presence of one or more modified nucleotides comprising a molecular tag; and
(e) Capturing the modified oligonucleotide/plasmid complex using the molecular tag/capture tag.

In a further preferred embodiment the method of the invention may be used for the selection of enzymes which act directly on a substrate molecule linked to an oligonucleotide and convert them to a product, which subsequently allows capture of the product/oligonucleotide/plasmid complex.

In yet a further preferred embodiment of the above aspect of the invention, the method of the invention may be used for the selection of enzymes which do not readily act on substrate molecules linked to an oligonucleotide. In this case the substrate is free to diffuse within a compartment according to the invention. The substrate is however linked to caged biotin and the product may be captured (after uncaging) by a streptavidin-oligonucleotide hybrid. Alternatively, product or products generated by the enzyme may result (directly or indirectly) in the modification of an oligonucleotide, for example using H2O2, HRP biotin tyramide) and/or the modification of antenna molecules (scavenger molecules) linked to the oligonucleotide.

As described above, the method for the invention may be used for the selection of enzymes which are not involved in nucleic acid processing directly but which modulate the functional activity of an enzyme, or by modulating the functional activity of an inhibitor of the enzyme.

Thus, in an alternative embodiment of the above aspect of the invention, there is provided a method for the selection of an enzyme which is indirectly involved in nucleic acid processing wherein the method is not dependent on the complete replication of the nucleic acid processing enzyme encoding gene and wherein the method comprises the steps of:
(a) Providing one or more nucleic acids molecules in the form of plasmids encoding one or more enzymes which are indirectly involved in nucleic acid processing, wherein the parent plasmid/s provides the gene sequence of the selected nucleic acid processing enzyme of interest.
(b) Compartmentalising those plasmids according to step (a), such that each compartment comprises a plasmid together, one or more enzymes encoded by the plasmid, one or more modified substrates of the enzyme encoded by the plasmid and one or more nucleic acid processing enzymes,
(c) Providing conditions such that stable association of an oligonucleotide specific for a region on the plasmid according to step (a) with that region of the plasmid is capable of occurring within that compartment;
(d) Providing conditions such that extension of the 3' end of the oligonucleotide according to step (a) using the nucleic acid processing enzyme in the presence of one or more modified nucleotides comprising a molecular tag is capable of occurring; and
(e) Capturing any one or more resultant 3' extended oligonucleotide/plasmid complexes using the molecular tag of step (d).

According to the above embodiment of the method of the invention, 'an enzyme which is indirectly involved in nucleic processing' includes those which are involved in the production of nucleic acid processing enzyme substrates from a blocked or inactive substrate. In this embodiment of the above aspect of the invention, in the case that an enzyme which is effective in the generation of active polymerase substrate is expressed within a particular compartment, then modification of an oligonucleotide according to the method of the invention using an active nucleic acid processing enzyme which is also present within that compartment in the presence of one or more modified nucleotides comprising a molecular tag is capable of occurring; and the subsequent selection of a plasmid/oligonucleotide complex may then take place using the molecular tag.

'An enzyme which is indirectly involved in nucleic acid processing' also includes within its scope those enzymes which are involved in the functional inactivation of one or more inhibitors of a nucleic acid processing enzyme. In this way, when an enzyme is expressed within a compartment which is capable of functionally inactivating one or more nucleic acid processing enzyme inhibitors, then modification of an oligonucleotide according to the method of the invention using an active nucleic acid processing enzyme which is also present within that compartment in the presence of one or more modified nucleotides comprising a molecular tag is capable of occurring; and the subsequent selection of a plasmid/oligonucleotide complex may then take place using the molecular tag.

In an alternative embodiment of the invention the method involves the use of a nicked double stranded plasmid and no separate oligo. Where the enzyme is a ligase, one selects for un-nicked plasmids (for example by intercalating nicked plasmids with EtBr and sucrose density centrifugation to separate nicked and un-nicked plasmids). Where the enzyme is a polymerase, one performs polymerisation (eg, where only one base is missing between the ends of the nicked strand) in the presence of a ligase. Again, un-nicked plasmids are selected. For tagging (eg, with biotin), one adopts a similar approach, the label being added to an end next to the nick.

Those skilled in the art will be aware of other procedures for using the method of the invention for the selection of enzymes which are indirectly involved in nucleic acid processing.

Those skilled in the art will appreciate that the method of the invention allows multiple rounds of selection to be performed without the need for reamplification and recloning, simply by capturing plasmid and retransformation. This reduces both time and the level of background mutations of the selection process. Alternatively, the gene of interest (or portions thereof) may be reamplified from captured plasmid and recloned.

Together with CSR and spCSR, CST should provide a full spectrum of selection stringency for polymerase activity and processivity ranging from distributive single turnover catalysis typical of poly polymerases like *E. coli* poly to the highly processive 1000 bases/sec catalytic proficiency of the replisome. According to the invention described herein, importantly, whilst CSR requires replication of the entire gene (usually >1000 bp) encoding the polymerase (or other enzymatic) activity and spCSR required replication of part of it (usually >50 bp), CST should require as little as a single incorporation event.

It is an essential feature of the invention that the one or more polymerases of interest are expressed from nucleic acid comprising a plasmid. In this way polymerase expression may be performed within cells as opposed to the in vitro transcription/translation systems discussed above. In this way both the problems discussed above relating to in vitro transcription/translation systems and those encountered in expressing polymerases from linear DNA are overcome.

The present inventors have performed extensive experiments aimed at optimising conditions to improve the efficiency of plasmid capture and therefore enhancing the sensitivity of the technique. These experiments are described in detail in Examples 10 to 14 herein and also in the detailed description of the invention.

In particular the present inventors have found that the efficiency of plasmid capture may be increased using any one or more of the techniques in the list consisting of the following: by increasing the Tm of the oligonucleotide/plasmid hybrid; by extending the oligonucleotide by more than 3 bases; by the use of a linker more than 40 atoms long between the molecular tag and the oligonucleotide and by the use of a oligonucleotide more than 10 bases long.

More specifically, according to the experiments performed by the inventors, the efficiency of plasmid capture is increased by increasing the Tm of the oligonucleotide/plasmid hybrid using any bases in the list consisting of the following: LNA bases and other suitable base types. Advantageously, the methods of the invention contemplate the use of LNA bases in order to increase the Tm of the oligonucleotide hybrid.

Other suitable bases for use according to the methods of the invention include but are not limited to diaminopurine (to replace A), G-clamps (Matteucci 99), LNA (Jepsen et al (2004), *Oligonucleotides*, 14, 130), INA (Christensen & Pedersen (2002), *Nucleic Acid Res*, 30, 4918) or any other base or backbone modifications that increase the Tm. Other possibilities to increase Tm include hybrid oligonucleotides (Ishihara & Corey 99), including DNA-PNA or DNA-peptide hybrids or covalent crosslinking to the template strand using a psoralen molecule stably incorporated into the oligonucleotide.

The present inventors have also found that the efficiency of plasmid capture is increased by extending the oligonucleotide by more than 20 bases. Advantageously, the efficiency of plasmid capture is increased by extending the oligonucleotide by more than 50 bases or more than 100 bases.

Further the present inventors have found that the efficiency of plasmid capture is increased by the use of a linker more than 50 atoms long between the molecular tag and the oligonucleotide. Advantageously, the efficiency of plasmid capture is increased by the use of a linker more than 70 atoms long between the molecular tag and the oligonucleotide. Most advantageously, the efficiency of plasmid capture is increased by the use of a linker more than 100 atoms long between the molecular tag and the oligonucleotide.

Definitions

The twin 'an oligonucleotide' refers to any sequence of single stranded nucleic acid. An oligonucleotide may be a partially or wholly artificial single stranded nucleic acid molecule consisting of exclusively synthetic or a mixture of naturally-occurring and synthetic bases, any one of the foregoing linked to a polypeptide, and any one of the foregoing linked to any other molecular group or construct. Advantageously, the other molecular group or construct may be selected from the group consisting of nucleic acids, polymeric substances, particularly beads, for example polystyrene beads, magnetic substances such as magnetic beads, labels, such as fluorophores or isotopic labels, chemical reagents, binding agents such as macrocycles and the like. According to the invention described herein, an oligonucleotide for use according to the method is capable of specific hybridisation with a region on a plasmid according to the method of the invention, either prior to modification of the oligonucleotide or subsequent to modification of the oligonucleotide. Advantageously, an oligonucleotide for use according to the method of the invention is capable of specific hybridisation with a region on a plasmid according to the method of the invention prior to modification of the oligonucleotide. According to the method of the present invention, one skilled in the art will appreciate that any oligonucleotide suitable for use according to the method of the invention must also be "extendable", e.g. have either from the start or after suitable processing a free and accessible 3' end.

The term 'modification of an oligonucleotide' according to the present invention refers to an alteration in the structure of the oligonucleotide. Such alterations include but are not limited to any one or more of the group consisting of the following: extension of the oligonucleotide (either 5' or 3'); ligation of the oligonucleotide to another entity, in particular a further oligonucleotide; phosphorylation of the oligonucleotide followed by tag ligation as herein described, conversion of an entity linked to the oligonucleotide to a different entity, for example conversion of a substrate linked to the oligonucleotide to a product; attachment of a molecular group to the oligonucleotide, for example $H_2O_2$, HRP biotin tyramide; the modification of antenna molecules/scavenger molecules linked to the oligonucleotide. According to the method herein described, modification of the oligonucleotide may be direct or indirect. However, in either case, it is an essential feature of the invention that the result of oligonucleotide modification is that a molecular tag/capture tag is incorporated into the oligonucleotide. This molecular tag/capture tag allows the subsequent capture of the enzyme/plasmid/oligonucleotide complex.

The term 'substrate processivity/processivity' means the number of nucleotides incorporated during a single cycle of binding primer-template duplex and extension before dissociation. As referred to herein, the term 'catalytic turnover/turnover' means the number of nucleotides incorporated into product in a certain amount of time In the inventor's experience, at low enzyme and or template concentrations processivity is important as binding of the substrate becomes the rate-limiting step. In contrast, at high enzyme and or template concentrations low processivity can at least partially be compensated by fast rebinding of enzyme to primer-template duplex.

'An enzyme which is indirectly involved in nucleic processing' includes those which are involved in the production of nucleic acid processing enzyme substrates from a blocked or inactive substrate. In this embodiment of the above aspect of the invention, in the case that an enzyme which is effective in the generation of active polymerase substrate is expressed within a particular compartment, then modification of an oligonucleotide according to the method of the invention using an active nucleic acid processing enzyme which is also present within that compartment in the presence of one or more modified nucleotides comprising a molecular tag is capable of occurring; and the subsequent selection of a plasmid/oligonucleotide complex may then take place using the molecular tag. 'An enzyme which is indirectly involved in nucleic acid processing' also includes within its scope those enzymes which are involved in the functional inactivation of one or more inhibitors of a nucleic acid processing enzyme. In this way, when an enzyme is expressed within a compartment which is capable of functionally inactivating one or more nucleic acid processing enzyme inhibitors, then modification of an oligonucleotide according to the method of the invention using an active nucleic acid processing enzyme which is also present within that compartment in the presence of one or more modified nucleotides comprising a molecular tag is capable of occurring; and the subsequent selection of a plasmid/enzyme/oligonucleotide complex may then take place using the molecular tag.

According to the present invention, the term 'compartment' is synonymous with the term 'microcapsule'. The structure and preparation of microcapsules is given in the detailed description of the invention.

The term (modification of the oligonucleotide) 'using the enzyme encoded by the plasmid is capable of occurring' includes within its scope the direct use of an enzyme encoded by the plasmid to incorporate a molecular tag into the oligonucleotide (for example the incorporation of tagged nucleotides into an oligonucleotide in the case where the enzyme is a nucleic acid replicase). In addition the term '(modification of the oligonucleotide) 'using the enzyme encoded by the plasmid is capable of occurring' includes within its scope the indirect use of an enzyme of interest to tag the oligonucleotide associated with the plasmid according to the method of the invention. Such indirect use would be for example, the conversion of a substrate linked to an oligonucleotide to a product in the presence of an enzyme encoded by the plasmid. In this case the 'molecular tag/capture tag' as herein defined is the product.

The term 'stable association' (of an oligonucleotide specific for a region on the plasmid with the plasmid) refers to the stable hybridisation of an oligonucleotide with the plasmid such that a plasmid encoding the enzyme of interest may be captured using the molecular tag present on the oligonucleotide.

BRIEF DESCRIPTION OF THE FIGURES

FIGS. 1A, 1B: Scheme of CST selection:
1) Hybridization: Bacterial cells expressing polymerase from a suitable vector (e.g. plasmid) are compartmentalized as previously described for CSR (Ghadessy et al 01) with reagents required for polymerase reaction (1× polymerase reaction buffer, dNTPs) and a CST primer and a tagged nucleotide (e.g. Biotin-16-dUTP). The CST primer is complementary to a sequence anywhere on the plasmid vector (and may or may not contain modifications such as an affinity enhancing peptide tag). A thermal denaturation step (e.g. 94° C. 5 min) releases plasmid and polymerase from the bacterial cell, denatures background polymerase activities and melts the plasmid DNA double strand so the CST primer can hybridize to its target sequence. An annealing step (e.g. 50° C. 5 min) allows the CST primer to anneal to its target sequence.
2) Tagging: An extension step (e.g. 72° C. 1-5 min) allows extension of the CST primer and incorporation of one or multiple tagged nucleotides.
3) Capture: After breaking of the emulsion (as previously described for CSR (Ghadessy et al 01)) the plasmid-extendedCSTprimer complex is isolated and captured on a solid-surface (e.g. Streptavidin coated magnetic beads) by virtue of the biotin moieties incorporated in the primer extension reaction. Plasmids not containing any biotin tags (and therefore reflecting compartments where there was no primer extension and hence no active polymerase) are washed away. Washing conditions are optimized so as to minimize dissociation of the CST-primer extension product from the plasmid.
4) Elution: Captured plasmids are either eluted from the beads and directly retransformed. For higher sensitivity, selected polymerase genes (residing on captured plasmids) are amplified preferably directly from the magnetic beads or alternatively from eluted plasmids and recloned for another round of CST selection.

A: Their hybridization is stabilized in the presence of two bait and prey fusion proteins, i.e. a receptorY-bait and receptor X-prey only if bait and prey interact.

B: Molecule (Y) for which there is a suitable high affinity receptor (receptorY) available is attached to the end of an oligonucleotide, which is too short to stably hybridize to the plasmid on its own. The oligonucleotide also bears a capture tag (e.g. biotin). Hybridization is stabilized in the presence of two bait and prey fusion proteins, i.e. a receptorY-bait and DBD-prey only if bait and prey interact. DBD denotes a DNA binding domain capable of either specific recognition of a suitable nearby target sequence or capable of sufficient non-specific DNA binding to stabilize the complex.

FIG. 5 PCR detection of captured plasmid in CST

A: CST test reaction +/− polymerase in solution.

Amount of captured plasmid is detected by PCR amplification of the bla gene directly from washed Dynabeads. − denotes reaction in the absence of 2.5 U of Taq polymerase, + denotes reaction in the presence of 2.5 U of Taq polymerase. "Input" denotes the CST reaction captured on beads prior to washing, "wash" denotes supernatant of second bead wash.

B CST using 2 different primers: 24G (left panel) & oligo 3 (right panel)

Amount of captured plasmid is detected by PCR amplification of the bla gene directly from washed Dynabeads. − denotes reaction in the absence of 2.5 U of Taq polymerase, + denotes reaction in the presence of 2.5 U of Taq polymerase.

The results show that CST is independent on where on the plasmid the CST primer hybridizes to.

Figure 6:
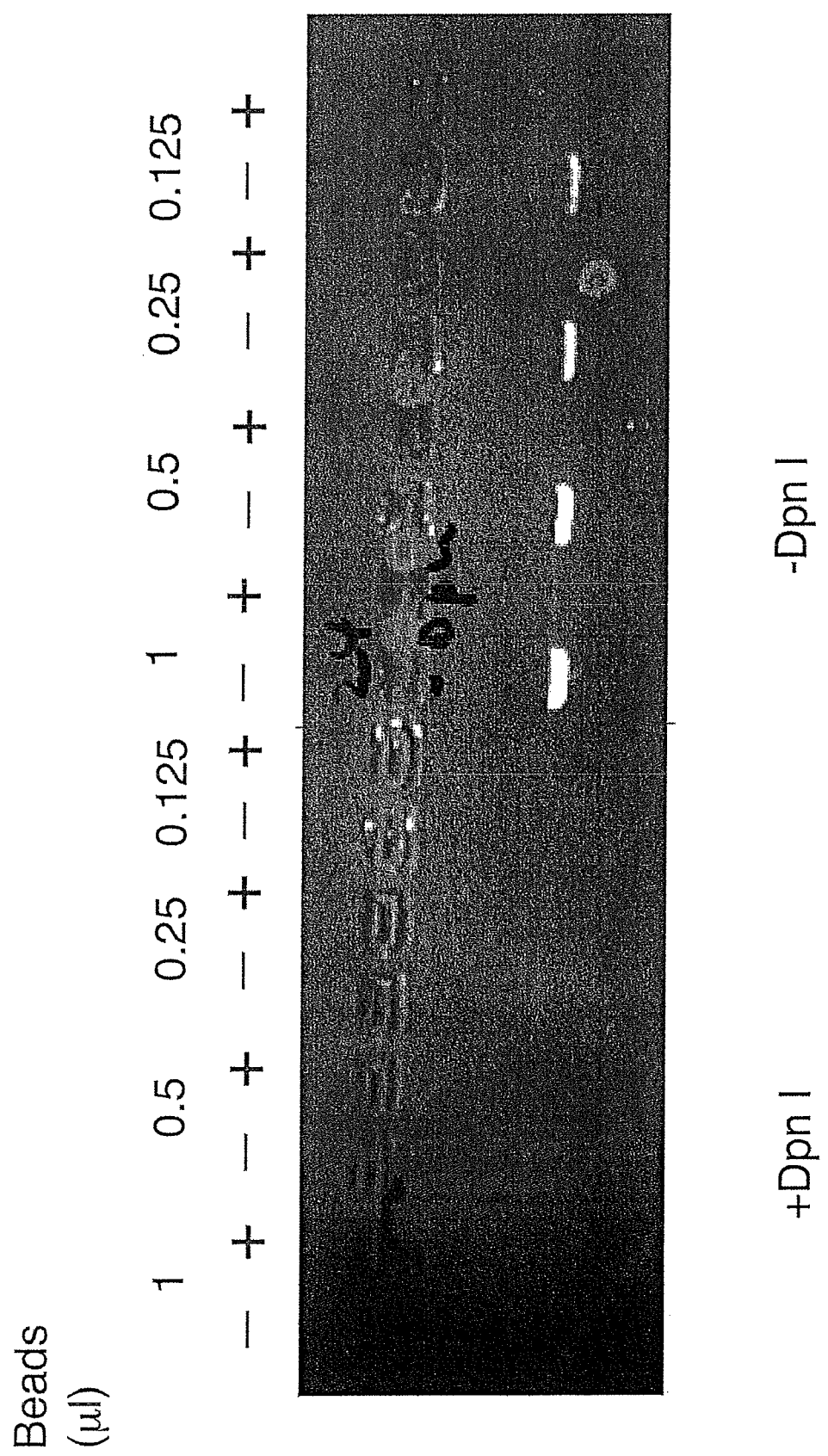

FIG. 6 PCR detection of captured plasmid II in CST

Control experiment to test that amplification band derives from captured plasmid on not from captured primer extension product. Dpn digest only dam methylated DNA such as plasmids replicated in a dam$^+$ strain.

Amount of captured plasmid is detected by PCR amplification of the bla gene directly from washed Dynabeads. − denotes reaction in the absence of 2.5 U of Taq polymerase, + denotes reaction in the presence of 2.5 U of Taq polymerase. Beads are preincubated with (left panel) or without (right panel) DpnI prior to amplification. Dpn almost completely abolishes amplification of the bla gene indicating that the amplification product observed derives overwhelmingly from captured plasmid and not from captured primer extension product.

Figure 7:
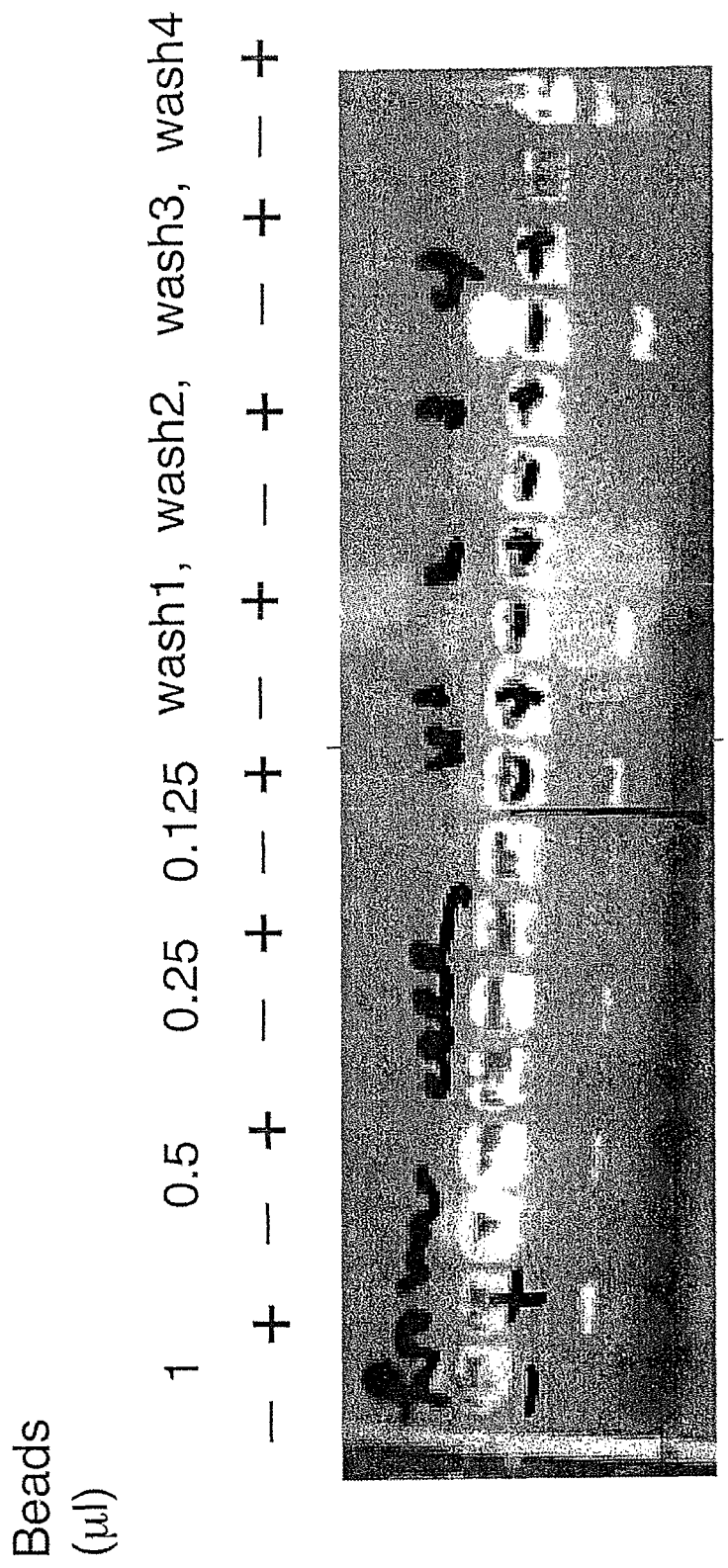

FIG. 7 PCR detection of captured plasmid III in CST

Control experiment to test that CST works with both plasmid and active Taq polymerase deriving from bacterial cells. Amount of captured plasmid is detected by PCR amplification of the bla gene directly from washed Dynabeads. − denotes reaction in the absence of 0.25 mM dNTP (final conc.), + denotes reaction in the presence of 0.25 mM dNTP (final conc.). Results show that plasmid is captured only in the presence of dNTP substrate.

Right panel shows control amplification from supernatant of the bead wash fractions. It shows that non-tagged plasmid adheres non-specifically to the beads but is washed off efficiently while tagged palsmid is not. (Wash 1 & 2: BBB wash, wash 3 & 4: 10 mM Tris pH8 wash).

Figure 8:
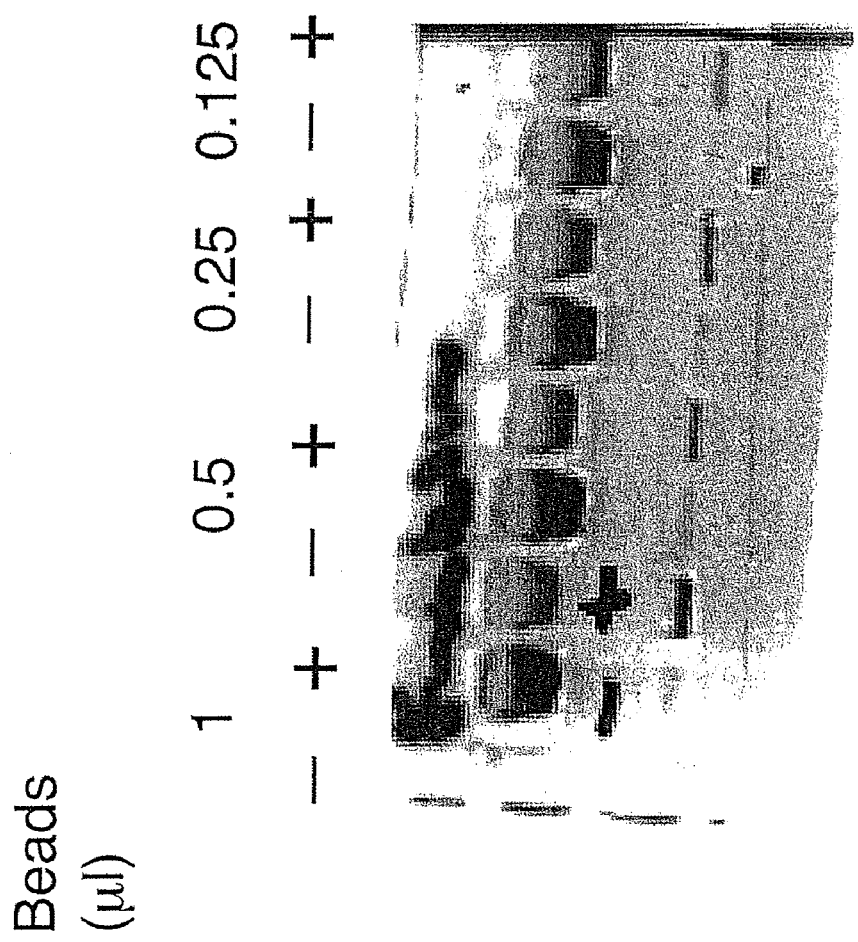

FIG. 8 CST in emulsion: PCR detection of captured plasmid III

Control experiment to test that CST works with both plasmid and active Taq polymerase deriving from bacterial cells in emulsion. Amount of captured plasmid is detected by PCR amplification of the bla gene directly from washed Dynabeads. − denotes reaction in the absence of 0.25 mM dNTP (final conc.), + denotes reaction in the presence of 0.25 mM dNTP (final conc.). Results show that plasmid is captured only in the presence of dNTP substrate.

Figure 9A:
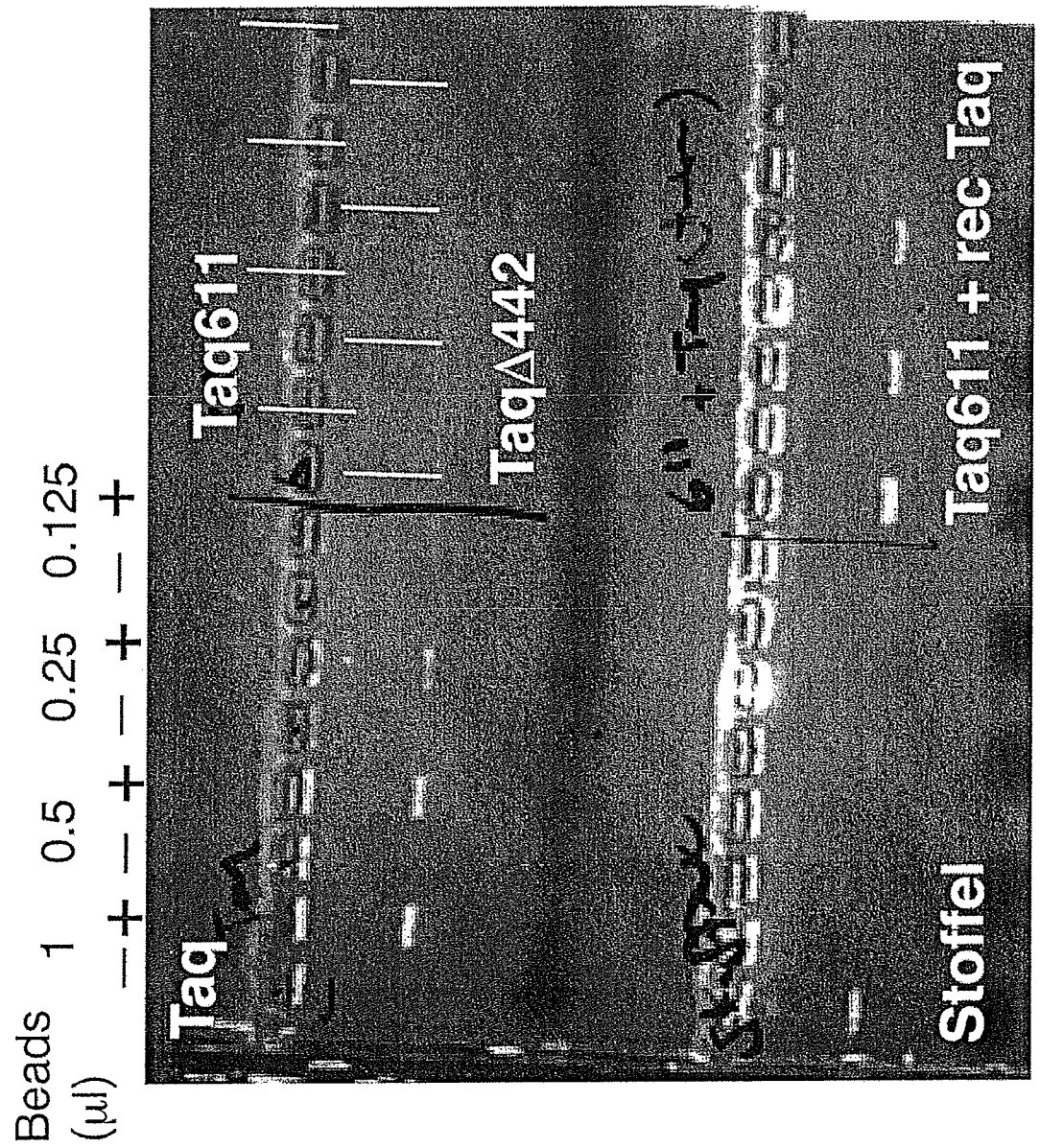
Figure 9B:
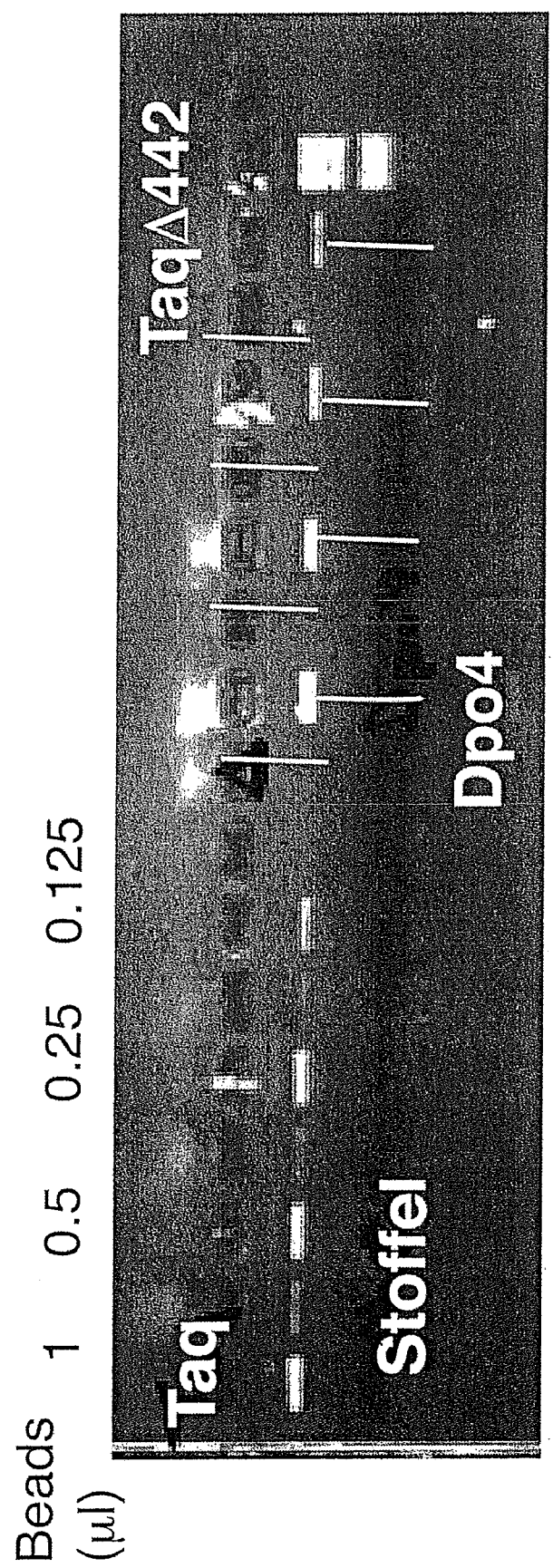

FIG. 9 Comparison of capture efficiency of different polymerases in CST

A, B: Control experiment to test capture efficiency of different polymerases in CST. Expressed polymerases and encoding plasmid derive from bacterial cells. Amount of captured plasmid is detected by PCR amplification of the bla gene directly from washed Dynabeads. − denotes reaction in the absence of 0.25 mM dNTP (final conc.), + denotes reaction in the presence of 0.25 mM dNTP (final conc.). Results show that active Taq polymerase and the less-processive Taq Stoffel fragment and Dpo4 (from S. solfataricus P2 (B)) are captured while the instable deletion variant Taq Δ442 and the inactive Taq 611 are not. Capture of inactive Taq 611 is rescued by addition of exogenous Taq polymerase (2.5 U).

Figure 10A:
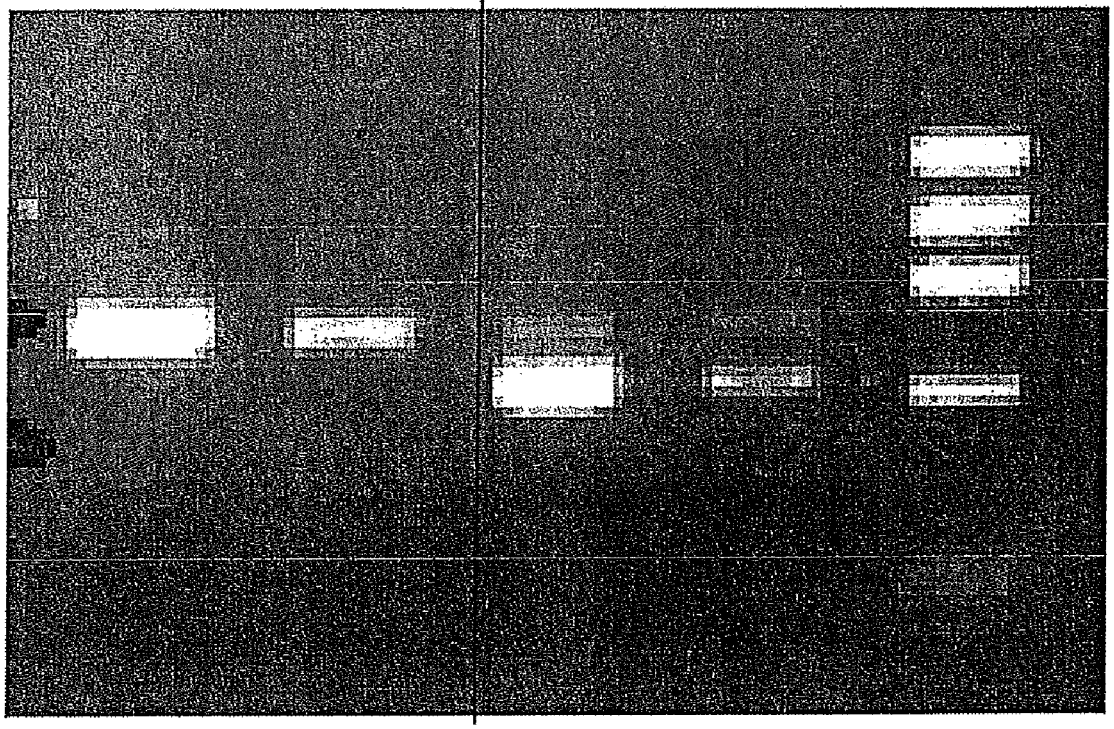

FIG. 10 CST selection of active polymerase (Taq wt) vs inactive polymerases (Taq 611)

A: Control experiment to test selection efficiency of active polymerase (Taq wt) vs inactive polymerases (Taq 611) in CST in emulsion. Amount of captured plasmid is detected by PCR amplification of part of the Taq gene directly from washed Dynabeads. $1/10^2$ and $1/10^3$ denotes that bacteria expression Taqwt are spiked into 1/100 or 1/1000 excess of bacteria expression Taq611a prior to selection. Taq611 contains an unique Bgl II in the amplified segment of the Taq gene. Amplification products prior to (left panel) and post Bgl II incubation (right panel) are resolved. Presence of the lower band indicates the amount of Taq611 gene in the amplification products.

Results show that active Taq polymerase is enriched to approx 1/10 in the 1/100 spike and to approx 1/3 in the 1/1000 spike. As seen with CSR selection efficiency is greater at greater dilution (presumably because of the reduction of the fraction of compartments comprising two cells one of which is contains active Taqwt).

B: Control experiment to test selection efficiency of active polymerase (Taq wt) vs inactive polymerases (Taq 611) in CST in emulsion. Taqwt are spiked into $1/10^4$ or $1/10^6$ excess of bacteria expression Taq611 a prior to selection. Selection efficiency is scored by determining the number of active Taq clones (in PCR) post CST selection There are 47/95 active clones after selection for the $10^4$-spike and 21/95 active clones after selection for the $10^6$-spike, Taq denotes Taqwt control. Active Taq polymerase is enriched over inactive Taq611 by CST by a factor of $>10^4$.

Figure 11:
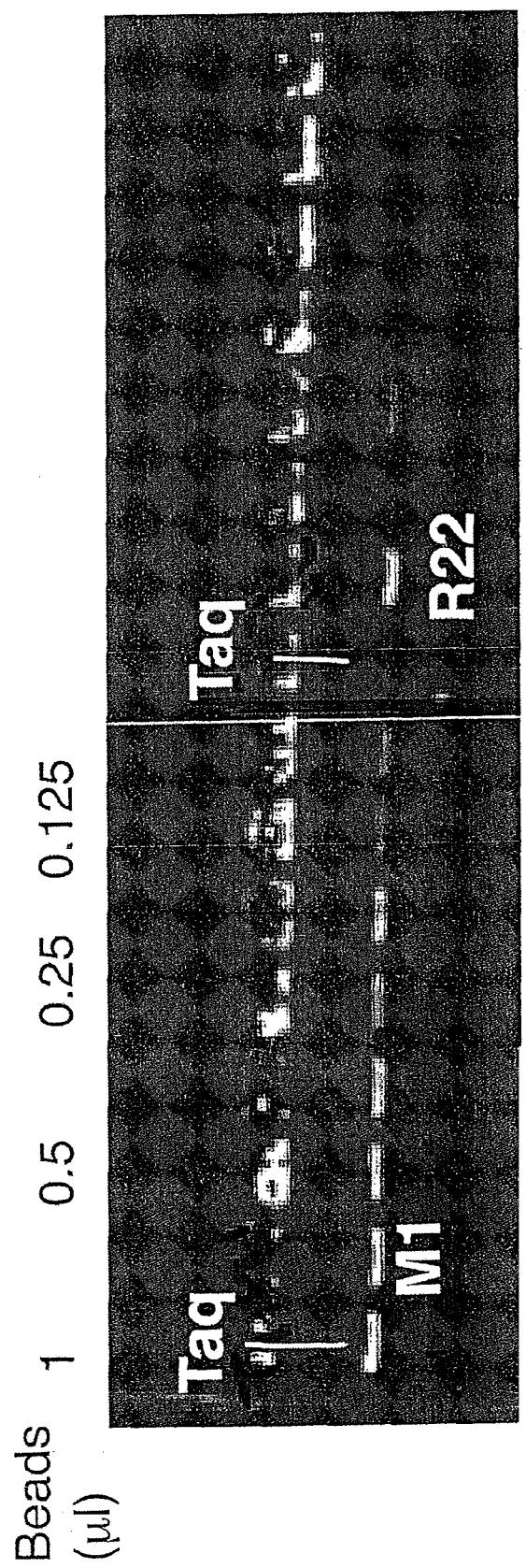

FIG. 11 Discrimination of substrate specificity by CST

Control experiment to test capture efficiency of different polymerases in CST depending on substrate specificity. Expressed polymerases and encoding plasmid derive from bacterial cells. Amount of captured plasmid is detected by PCR amplification of the bla gene directly from washed Dynabeads. − denotes reaction in the absence of 0.25 mM dNTP (final conc.), + denotes reaction in the presence of 0.25 mM dNTP (final conc.).

Left panel: Discrimination of capture efficiency in CST in which the CST primer has a 5-nitroindole base analogue as its 3' base. Results show that Taq mutant M1 displays an increased ability to extend from a primer bearing a 5-nitroindole in CST compared to Taqwt as previously known.

Right panel: Discrimination of capture efficiency in CST in which dATP is replaced by ATP. Results show that Taq mutant R22 shows much increased, although weak capture compared to Taqwt. R22 was known to be able to incorporate ribonucleotides with much increased efficiency.

Figure 12:
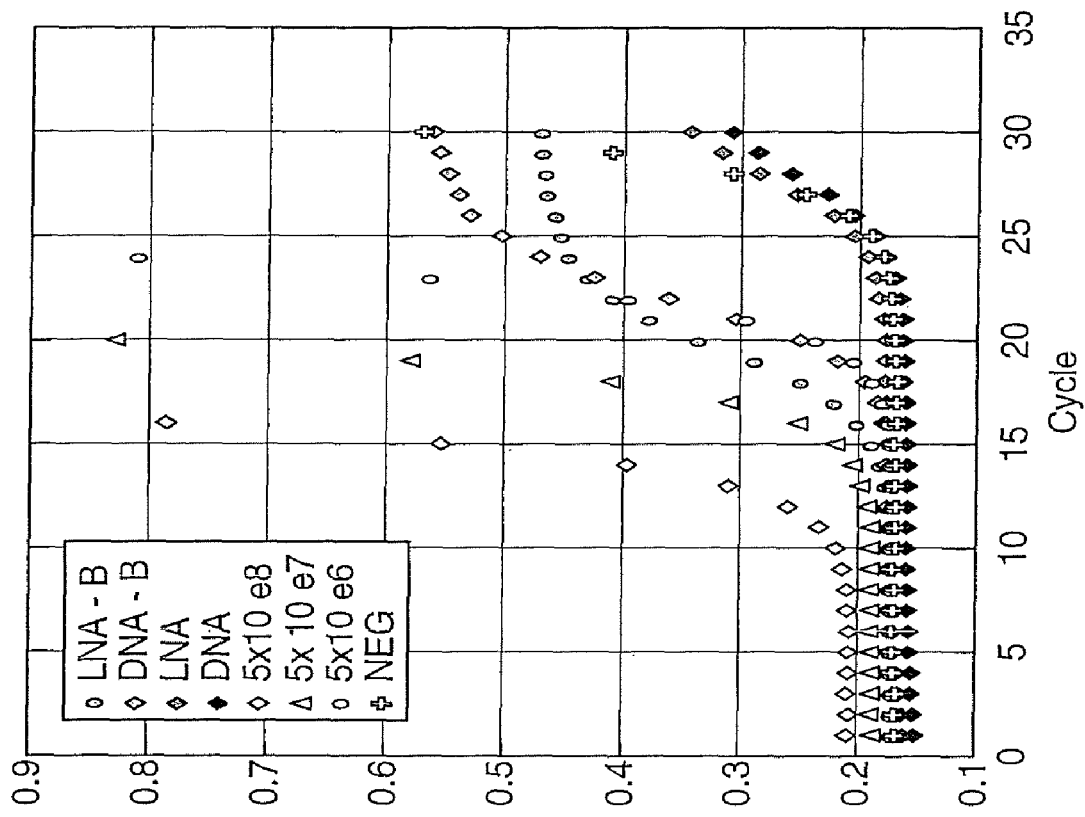
Figure 12:
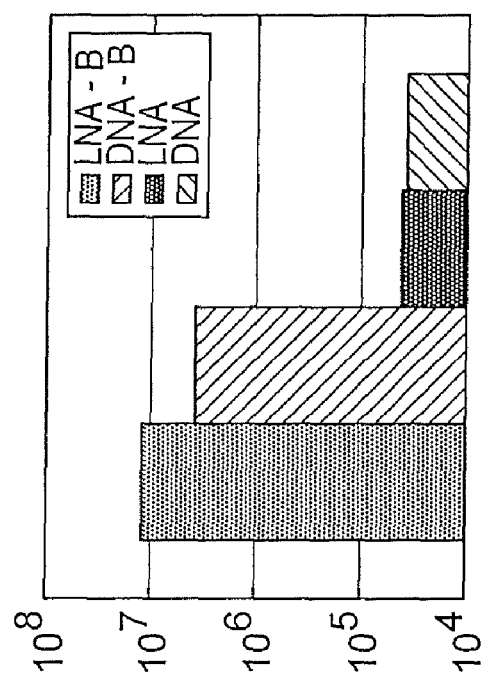

FIG. 12. LNA-B—5' biotinilated oligonucleotide with 44% LNA bases, LNA—non biotinilated oligonucleotide with 44% LNA bases, DNA-B—5' biotinilated DNA oligonucleotide (24G—with a G-clamp), DNA—non-biotinilated DNA oligonucleotide 24G. A. Calculated number of plasmid molecules captured with each primer, B—example of raw data obtained with the qPCR.

Figure 13:
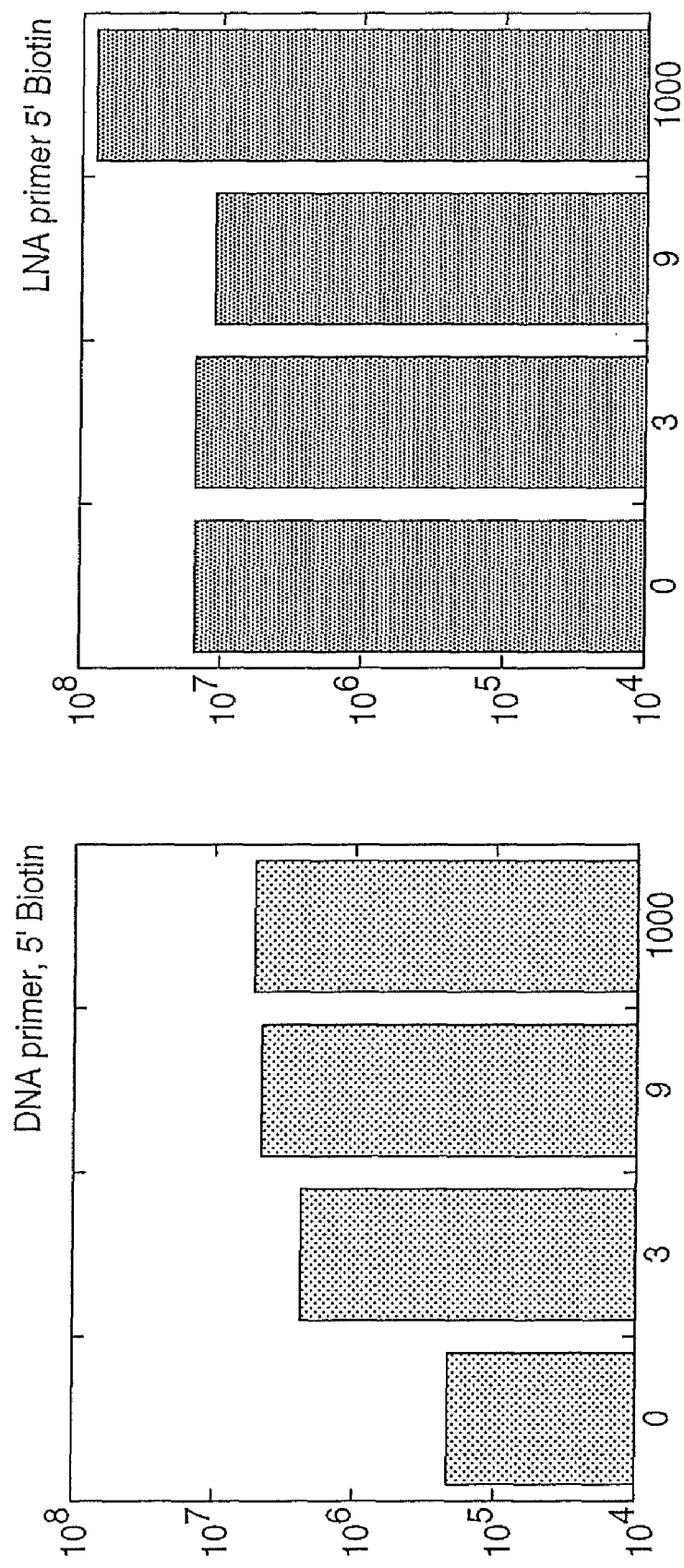

FIG. 13. Effect of the extension length on plasmid capture with the use of LNA-DNA oligonucleotide (A) and DNA only oligonucleotide (B). 0—no extension, 3—extension by 3 bases, 9—extension by 9 bases, 1000—full extension (hundreds to thousands of bases).

Figure 14:
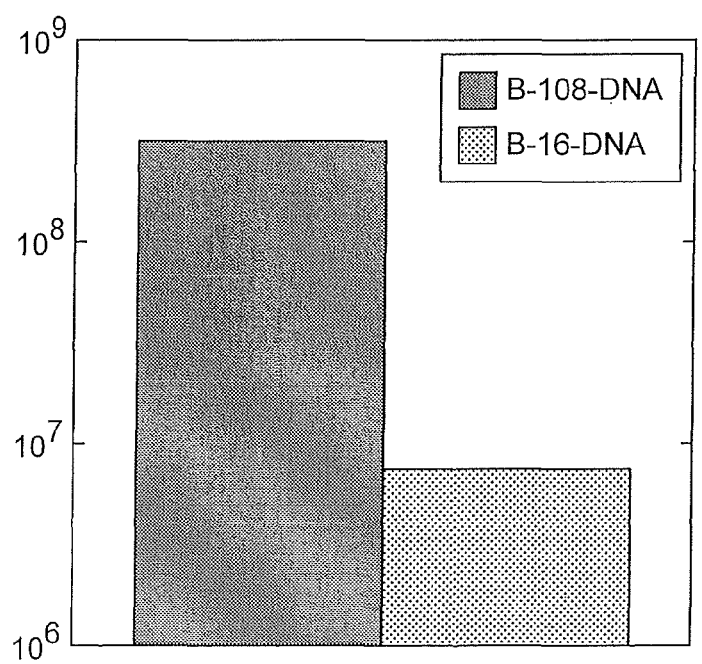

FIG. 14. Efficiency of the plasmid capture with the use of 5' biotinilated primer with a 108 atom linker between biotin and a base (B-108-DNA) and a 5' biotinilated primer with a 16 atom linker between biotin and a base (B-16-DNA). 108B primer 5'-Biotin-108 atom linker-GATCTTCACCTA-GATCCT-3'.

Figure 15:
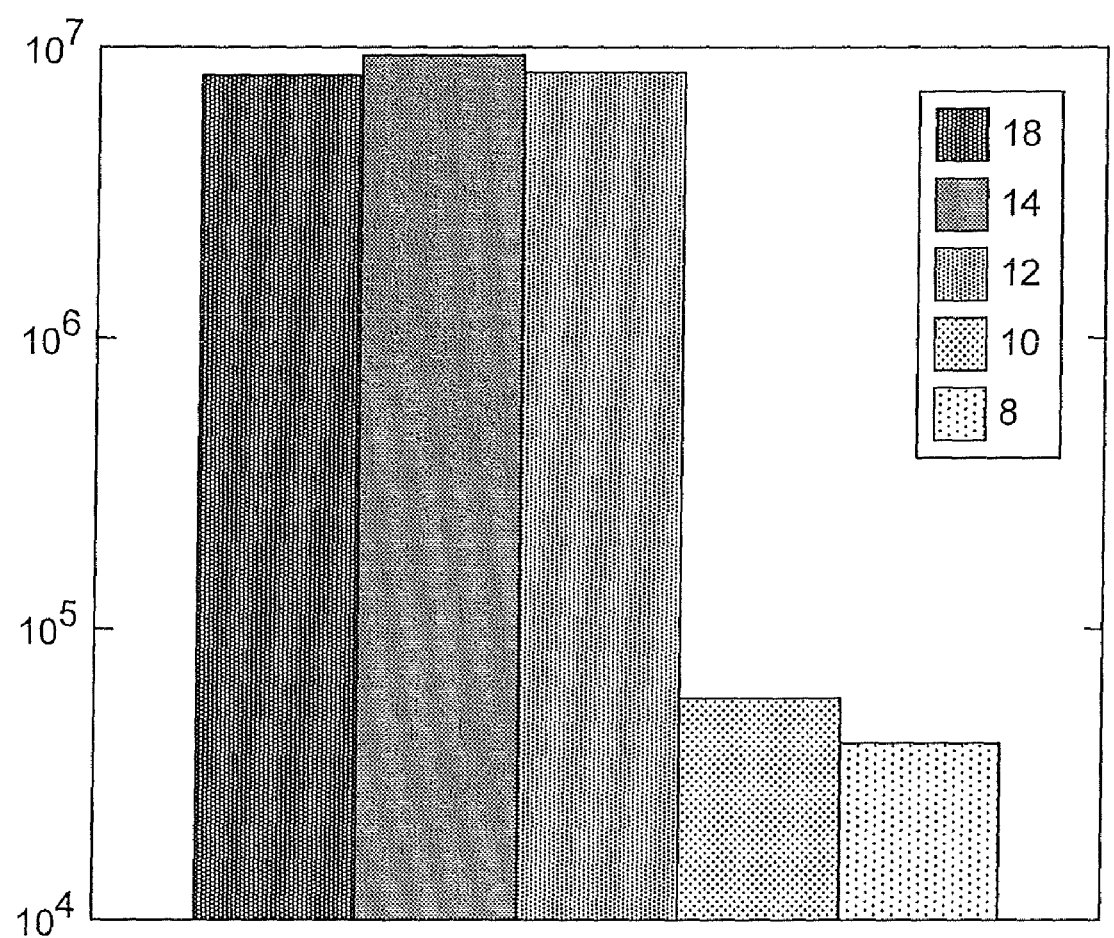

FIG. 15. The effect of the length of the primer on the capture efficiency.

DETAILED DESCRIPTION OF THE INVENTION (A) General Strategy of the Method of the Invention
A Method for the Selection of an Enzyme Capable of Directly or Indirectly Modifying an Oligonucleotide.

In a first aspect the present invention provides a method for the selection of an enzyme capable of directly or indirectly modifying an oligonucleotide wherein the method is not dependent on the complete replication of the oligonucleotide modifying enzyme encoding gene, which method comprises the steps of
(a) Providing one or more nucleic acid molecules in the form of parent plasmids encoding one or more enzymes of interest, wherein the parent plasmid provides the gene sequence of the selected enzyme of interest.
(b) Compartmentalising those plasmids according to step (a), such that each compartment comprises a plasmid together with the one or more enzymes encoded by the plasmid and an oligonucleotide specific for a region on the plasmid according to step (a).
(c) Providing conditions such that stable association of the oligonucleotide according to step (b) with a region of the plasmid is capable of occurring;
(d) Providing conditions such that modification of the oligonucleotide according to step (b) using the enzyme encoded by the plasmid is capable of occurring and such that the resultant modified oligonucleotide comprises a molecular tag; and
(e) Capturing the modified oligonucleotide/plasmid complex.

The method of the invention may be summarised in its simplest form by several steps:
Expression of an enzyme of interest from plasmids, preferably in whole cells.
Hybridisation of an oligonucleotide specific for the plasmid to that region of a plasmid
Modification of that oligonucleotide in the presence of the enzyme of interest.
Capture of the modified oligonucleotide/plasmid via the use of the tag.

The method of the invention has several important features:
Importantly, the use of plasmids to express the enzyme of interest means that such expression may occur within whole cells which comprise all the machinery required for the expression and processing of the enzyme of interest. Therefore according to the method of the invention there is no requirement for the use of in vitro transcription/translation systems.

Furthermore by expressing the enzyme of interest from plasmids, many of the problems posed by attempting such a selection method using linear DNA are overcome. For example, the in situ expression of polymerases (inside compartments) from a linear DNA fragment in an in vitro transcription/translation system (ivt) in the presence of biotinylated nucleotides (Bio-dNTP) results, in the inventor's experience in a high background of tagging of the 3' ends of the linear fragment with Bio-dNTP regardless of the activity of the expressed polymerase and regardless of the nature of the 3' end (5' overhang, blunt, or 3' overhang).

Furthermore the method of the invention has several important advantages over the CSR method previously described by the present inventors.

'An Oligonucleotide'

According to the method described herein the term 'an oligonucleotide' refers to any sequence of single stranded nucleic acid. An oligonucleotide may be a partially or wholly artificial single stranded nucleic acid molecule consisting of exclusively synthetic or a mixture of naturally-occurring and synthetic bases, any one of the foregoing linked to a polypeptide, and any one of the foregoing linked to any other molecular group or construct. Advantageously, the other molecular group or construct may be selected from the group consisting of nucleic acids, polymeric substances, particularly beads, for example polystyrene beads, magnetic substances such as magnetic beads, labels, such as fluorophores or isotopic labels, chemical reagents, binding agents such as macrocycles and the like. According to the invention described herein, an oligonucleotide for use according to the method is capable of specific hybridisation with a region on a plasmid according to the method of the invention, either prior to modification of the oligonucleotide or subsequent to modification of the oligonucleotide. Advantageously, an oligonucleotide for use according to the method of the invention is capable of specific hybridisation with a region on a plasmid according to the method of the invention prior to modification of the oligonucleotide.

According to the method of the present invention, those skilled in the art will appreciate that the length of oligonucleotide suitable for use depends upon the selection conditions and also the GC content of the oligonucleotide. Advantageously, an oligonucleotide suitable for use according to the method of the invention will greater than 10, 11, 12, 13, 14, 15, 16, 17, 18, 19, 20 nucleotides long.

'Modification of an Oligonucleotide'

The term 'modification of an oligonucleotide' refers to an alteration in the structure of the oligonucleotide. Such alterations include but are not limited to any one or more of the group consisting of the following: extension of the oligo (either 5' or 3'); ligation of an oligonucleotide to another entity, in particular a further oligonucleotide; phosphorylation of the oligonucleotide followed by tag ligation as herein described, conversion of a entity linked to the oligonucleotide to a different entity, for example conversion of a substrate linked to the oligonucleotide to a product; attachment of a molecular group to the oligonucleotide, for example H2O2, HRP biotin tyramide; the modification of antenna molecules/scavenger molecules linked to the oligonucleotide.

According to the method herein described, modification of the oligonucleotide may be direct or indirect. However, in either case, it is an essential feature of the invention that the result of oligonucleotide modification is that a molecular tag/capture tag is incorporated into the oligonucleotide. This molecular tag/capture tag allows the subsequent capture of the enzyme/plasmid/oligonucleotide complex.

Molecular Tags/Capture Tags.

Those skilled in the art will appreciate that the details of the method of incorporation of molecular tags into an oligonucleotide according to the invention will depend upon the properties of the enzyme of interest.

(i) Tagged Nucleotides/Oligonucleotides

For example, in the case that the enzyme of interest is a DNA polymerase then incorporation of one or more tagged nucleotides into the 3' end of the DNA sequence is used to incorporate a capture tag/molecular tag into the genetic element using the DNA polymerase. Furthermore, in the case that the enzyme of interest is a ligase, then the molecular tag is incorporated into the oligonucleotide via the ligation of a second tagged oligonucleotide to the oligonucleotide which is associated with the plasmid according to the invention. Furthermore, in the case that the enzyme of interest is a polynucleotide kinase, then incorporation of a molecular tag occurs via the 5' phoshorylation and ligation of a second oligonucleotide which bears a molecular tag. Those skilled in the art will appreciate that this list is not intended to be exhaustive.

Figure 1B:
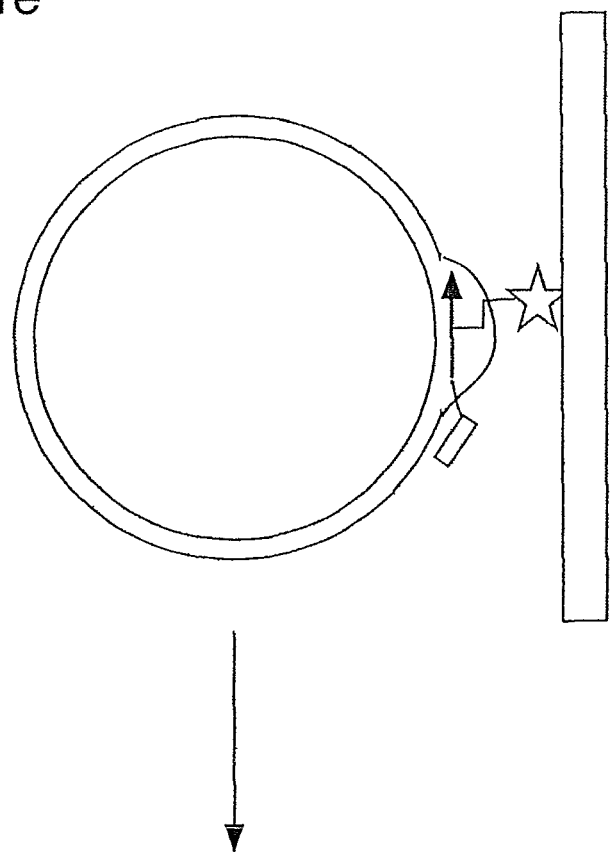

In the case where the molecular tag/capture tag is a tagged nucleotide, the nucleotide triphosphate mix within a compartment according to the invention is spiked with a (or several) nucleotides modified with a molecular tag, e.g. biotin-dUTP. After extension and incorporation, the plasmid-oligonucleotide complex becomes decorated with tag molecules (e.g. biotin), allowing its capture (FIGS. 1A, 1B).

Tagged nucleotides themselves may be unnatural substrates (such as e.g. an altered base like 5-nitroindole or a ribonucleotide) and thus their incorporation may select directly for the sought after phenotype. Alternatively, incorporation may be an indication of polymerase activity under the selection conditions or an ability to extend a modified 3' end.

Suitable molecular tags/capture tags include biotin, digoxigenin (DIG), fluorescein (FITC), di-nitrophenol (DNP) etc., which can be captured using avidin/streptavidin or suitable antibodies. Alternatively, the nucleotide may be modified to display a free amino group (NH2), which can be specifically modified post extension with a suitable tag. Those skilled in the art will appreciate that this list is not intended to be exhaustive and will be aware of other suitable molecular tags.

Multiple tags may offer the possibility of two (or multi-) step capture and selection schemes, or capture schemes with combinations of selection requirements, e.g. capture all molecules with A or B, or all molecules with A and B, or molecules with A but not B.

Product-Linked to Oligonucleotide as a Capture Tag.

In a further preferred embodiment the method of the invention may be used for the selection of enzymes which act directly on a substrate molecule linked to an oligonucleotide and convert them to a product, which subsequently allows capture of the product/oligonucleotide/plasmid complex. Thus according to this embodiment of the invention, the capture tag/molecular tag is the product linked to an oligonucleotide.

Enzymes for Selection According to the Method of the Invention.

The present inventors have found that the method of the invention is particularly suitable for the selection of enzymes, particularly nucleic acid processing enzymes which have any one or more of the following characterisitics: low catalytic turnover, low substrate processivity, nucleic acid processing enzymes which incorporate modified nucleotide substrates and polymerases with a high-error rate (approximately 1/N errors for a polymerase gene of N bases).

Suitable enzymes for selection using the method of the invention include any one or more of those selected from the group consisting of the following: nucleic acid processing enzymes, enzymes which act on one or more substrates of nucleic acid replicases (that is, enzymes indirectly involved in nucleic acid processing), enzymes which modulate the activity of replicases (that is, enzymes indirectly involved in nucleic acid processing), enzymes which act directly on a substrate molecule linked to an oligonucleotide wherein the oligonucleotide is capable of stable association with a region of a plasmid encoding that enzyme according to the method of the invention, enzymes which act indirectly on a substrate molecule linked to an oligonucleotide.

Suitable nucleic acid processing enzymes for use according to the method of the invention include any of those selected from the group consisting of the following: replicases, in particular DNA replicases; DNA ligases, RNA ligases, polynucleotide kinases.

In particular CST is useful for the selection of polymerases, which are naturally distributive or poorly processive, such as members of the polY or polX family or low-processivity variants of high processivity polymerases such as the Stoffel fragment of Taq polymerase or T7 DNA polymerase in the absence of thioredoxin. Alternatively, starting from a highly active and processive polymerase CST may allow evolutionary trajectories that are populated with variants of greatly reduced turn-over and/or processivity, such as are likely to be encountered when making changes to substrate or extension chemistry.

CST should also allow multiple rounds of selection to be performed without the need for reamplification and recloning, reducing both time and the level of background mutations of the selection process. Together with CSR and spCSR, CST should provide a full spectrum of selection stringency for polymerase activity and processivity ranging from distributive single turnover catalysis typical of polY or polX polymerases to the highly processive 1000 bases/sec catalytic proficiency of the replisome Plasmids Suitable plasmids for use according to the method of the invention will be familiar to those skilled in the art. Advantageously, they will be small plasmids, in the order of less than 10 kB and have a high copy number. Such plasmids include but are not limited to any one or more of the following: colE1 or p15 origin of replication such as derivatives of pUC, pBR322, pACYC184 or pACYC177.

Compartments/Microcapsules.

The microcapsules of the present invention require appropriate physical properties to allow the working of the invention.

First, to ensure that the genetic elements and gene products may not diffuse between microcapsules, the contents of each microcapsule must be isolated from the contents of the surrounding microcapsules, so that there is no or little exchange of the genetic elements and gene products between the microcapsules over the timescale of the experiment.

Second, the method of the present invention requires that there are only one type of genetic element per compartment. There can be multiple copies but they need be identical, i.e. each compartment contains a clone (one or many copies of one genetic element A but not a mixture of genetic elements A, B, C etc.) of genetic elements per microcapsule/compartment. This ensures that the gene product of an individual genetic element will be isolated from other genetic elements.

Thus, coupling between genetic element and gene product will be highly specific. The enrichment factor is greatest with on average one or fewer genetic elements per microcapsule, the linkage between nucleic acid and the activity of the encoded gene product being as tight as is possible, since the gene product of an individual genetic element will be isolated from the products of all other genetic elements. However, even if the theoretically optimal situation of, on average, a single genetic element or less per microcapsule is not used, a ratio of 5, 10, 50, 100 or 1000 or more genetic elements per microcapsule may prove beneficial in sorting a large library. Subsequent rounds of sorting, including renewed encapsulation with differing genetic element distribution, will permit more stringent sorting of the genetic elements.

Third, the formation and the composition of the microcapsules must not abolish the function of the machinery the expression of the genetic elements and the activity of the gene products.

Consequently, any microencapsulation system used must fulfil these three requirements. The appropriate system(s) may vary depending on the precise nature of the requirements in each application of the invention, as will be apparent to the skilled person.

A wide variety of microencapsulation procedures are available (see Benita, 1996) and may be used to create the microcapsules used in accordance with the present invention. Indeed, more than 200 microencapsulation methods have been identified in the literature (Finch, 1993).

These include membrane enveloped aqueous vesicles such as lipid vesicles (liposomes) (New, 1990) and non-ionic surfactant vesicles (van Hal et al., 1996). These are closed-membranous capsules of single or multiple bilayers of non-covalently assembled molecules, with each bilayer separated from its neighbour by an aqueous compartment. In the case of liposomes the membrane is composed of lipid molecules; these are usually phospholipids but sterols such as cholesterol may also be incorporated into the membranes (New, 1990). A variety of enzyme-catalysed biochemical reactions, including RNA and DNA polymerisation, can be performed within liposomes (Chakrabarti et al., 1994; Oberholzer et al., 1995a; Oberholzer et al., 1995b; Walde et al., 1994; Wick & Luisi, 1996).

Preferably, the microcapsules of the present invention are formed from emulsions; heterogeneous systems of two immiscible liquid phases with one of the phases dispersed in the other as droplets of microscopic or colloidal size (Becher, 1957; Sherman, 1968; Lissant, 1974; Lissant, 1984).

Emulsions may be produced from any suitable combination of immiscible liquids. Preferably the emulsion of the present invention has water (containing the biochemical components) as the phase present in the form of finely divided droplets (the disperse, internal or discontinuous phase) and a hydrophobic, immiscible liquid (an 'oil') as the matrix in which these droplets are suspended (the nondisperse, continuous or external phase). Such emulsions are termed 'water-in-oil' (W/O). This has the advantage that the entire aqueous phase containing the biochemical components is compartmentalised in discreet droplets (the internal phase). The external phase, being a hydrophobic oil, generally contains none of the biochemical components and hence is inert.

The emulsion may be stabilised by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash and Ash, 1993). Suitable oils include light white mineral oil and non-ionic surfactants (Schick, 1966) such as sorbitan monooleate (Span™ 80; ICI) and polyoxyethylenesorbitan monooleate (Tween™ 80; ICI).

The use of anionic surfactants may also be beneficial. Suitable surfactants include sodium cholate and sodium taurocholate. Particularly preferred is sodium deoxycholate, preferably at a concentration of 0.5% w/v, or below. Inclusion of such surfactants can in some cases increase the expression of the genetic elements and/or the activity of the gene products. Addition of some anionic surfactants to a non-emulsified reaction mixture completely abolishes translation. During emulsification, however, the surfactant is transferred from the aqueous phase into the interface and activity is restored. Addition of an anionic surfactant to the mixtures to be emulsified ensures that reactions proceed only after compartmentalisation.

Creation of an emulsion generally requires the application of mechanical energy to force the phases together. There are a variety of ways of doing this which utilise a variety of mechanical devices, including stirrers (such as magnetic stir-bars, propeller and turbine stirrers, paddle devices and whisks), homogenisers (including rotor-stator homogenisers, high-pressure valve homogenisers and jet homogenisers), colloid mills, ultrasound and 'membrane emulsification' devices (Becher, 1957; Dickinson, 1994).

Aqueous microcapsules formed in water-in-oil emulsions are generally stable with little if any exchange of genetic elements or gene products between microcapsules. Additionally, we have demonstrated that several biochemical reactions proceed in emulsion microcapsules. The technology exists to create emulsions with volumes all the way up to industrial scales of thousands of litres (Becher, 1957; Sherman, 1968; Lissant, 1974; Lissant, 1984).

The preferred microcapsule size will vary depending upon the precise requirements of any individual selection process that is to be performed according to the present invention. In all cases, there will be an optimal balance between gene library size, the required enrichment and the required concentration of components in the individual microcapsules to achieve efficient reactivity of the gene products.

Depending on the application, the mean volume of the microcapsules is less that $5.2\times10^{-16}$ m$^3$, (corresponding to a spherical microcapsule of diameter less than 10 μm, more preferably less than $6.5\times10^{-17}$ m$^3$ (5 μm), more preferably about $4.2\times10^{-18}$ m$^3$ (2 μm) and ideally about $9\times10^{-18}$ m$^3$ (2.6 μm).

The thermostable emulsions used in CSR or emulsion PCR have a mean diameter of 15 μm and this may be required for proper activity when compartmentalizing cells.

The microcapsule size must be sufficiently large to accommodate all of the required components of the biochemical reactions that are needed to occur within the microcapsule.

In the case of CST gene and expressed enzyme are colocalised using cells containing 100-500 copies of plasmid+ 1000-100000 copies of polymerase and cells are emulsified for example using 1× Taq buffer+0.2 mM dNTP concentration final.

Oligonucleotide Hybridization: Forming an Artificial Primosome

Hybridization requires the opening up of a region of duplex DNA and strand invasion of the oligonucleotide to anneal to one of the two strands of the melted duplex DNA "bubble". This structure can then act an artificial primosome for a DNA polymerase, which can extend further along the template strand (to which the oligo is annealed) until the next duplex region (or further through strand displacement).

Figure 1B:
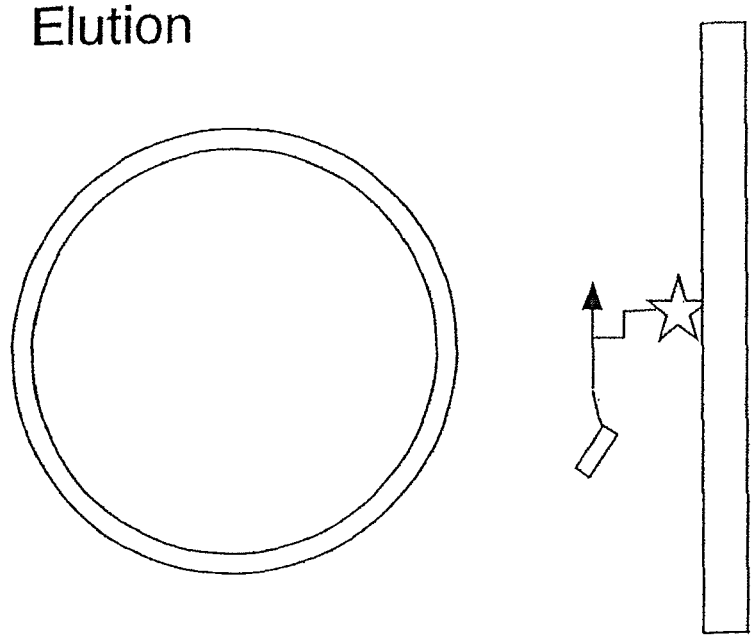
Figure 2:
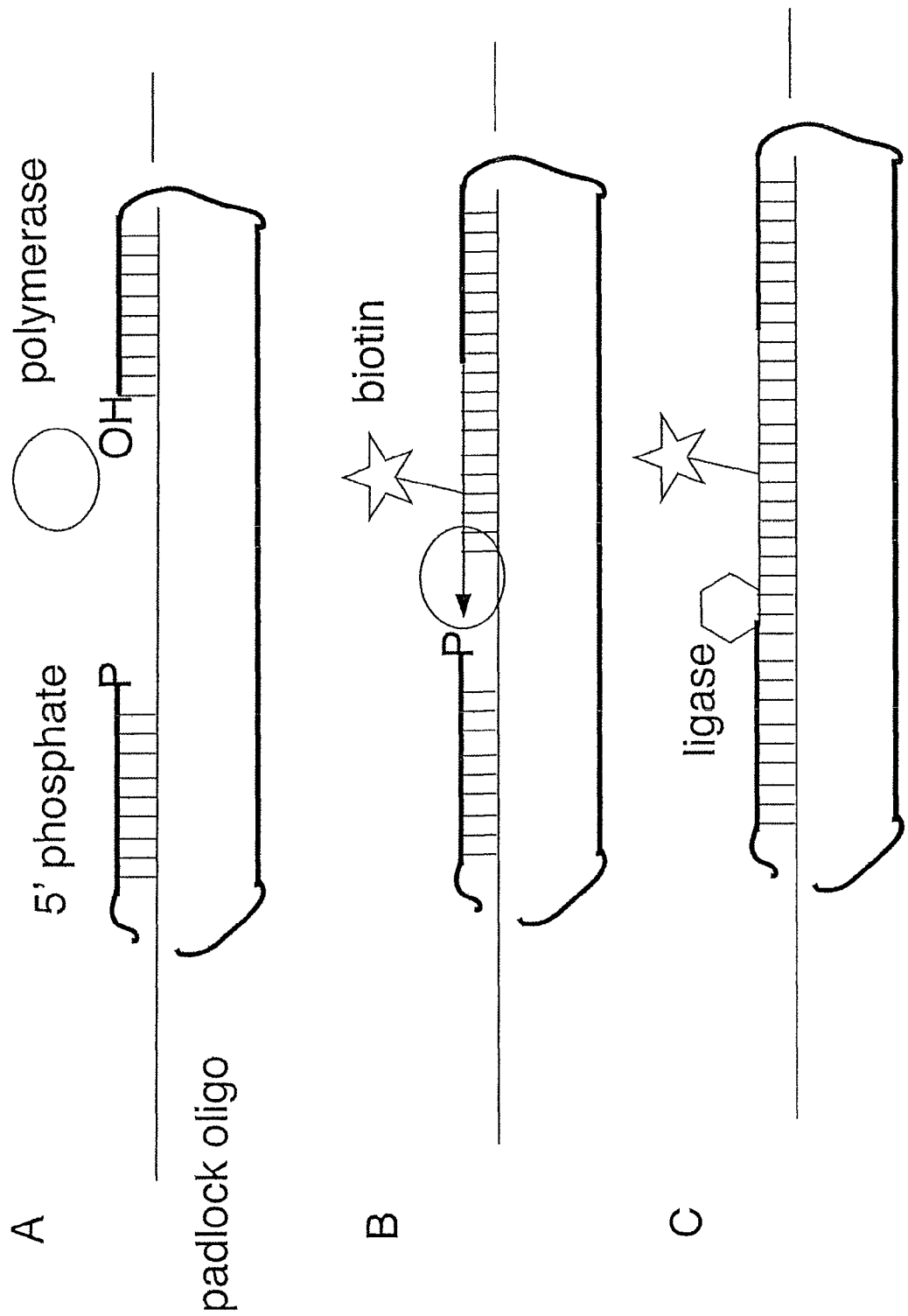
FIG. 2: A modification on the CST scheme of FIG. 1
A: In order to stabilize the CST primer extension product, the CST primer may be a "padlock" probe with a phosphorylated 5' end.
B: Thus primer extension incorporates tagged nucleotides and close the gap between padlock 3' and 5' end.
C: The padlock is then closed by DNA ligation. The closed padlock represents a non-dissociable plasmid-CST primer complex permitting stringent bead washing conditions (see FIG. 1)
Figure 3C:
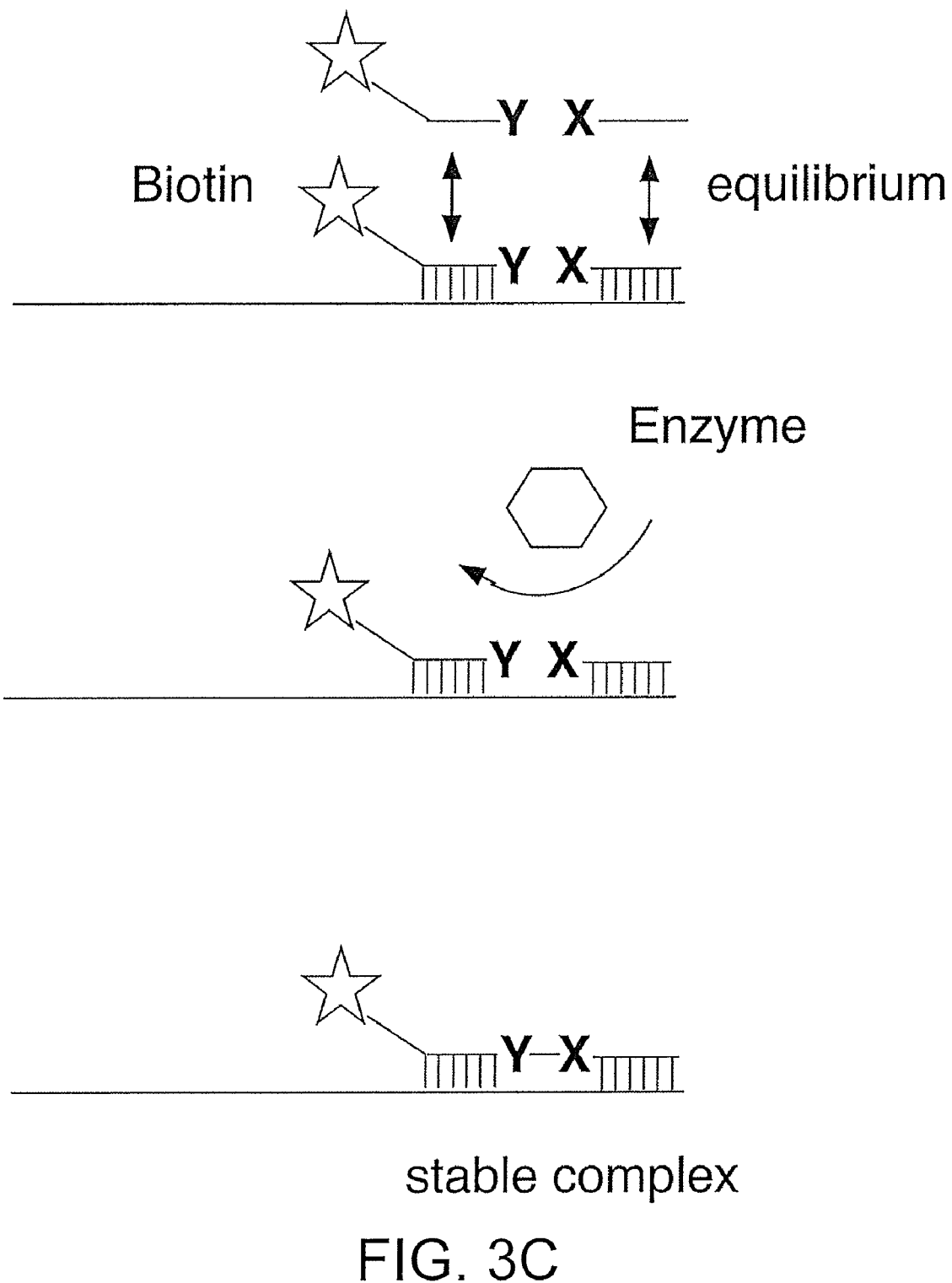
FIG. 3: CST selection of enzymatic activities other than polymerases
A: The substrate for the enzyme of choice (white hexagon) is attached to the 3' end of the CST primer and blocks extension by the polymerase. Active enzyme X converts substrate X creating an extendable 3' end (e.g. OH) at the CST primer terminus. Standard primer extension and CST selection follows.
B: The substrates (X & Y) for the enzyme of choice (white hexagon) are attached to the 3' ad 5' ends of two primers, each of which is too short to stably hybridize to the plasmid on its own and thus cannot be extended by the polymerase. Active enzyme reacts with X & Y linking the two primers and creating a stably hybridized CST primer extension of which allows CST selection to proceed.
C: The substrates (X & Y) for the enzyme of choice (white hexagon) are attached to the 3' and 5' ends of two oligonucleotides, each of which is too short to stably hybridize to the plasmid on its own. One oligonucleotide (or both) bears a capture tag (e.g. biotin). Active enzyme reacts with X & Y linking the two oligonucleotides and creating a stably hybridized oligonucleotide which allows capture and selection without the need for primer extension by a polymerase.
D: The substrates (X) for the enzyme of choice (white hexagon) are attached to an oligonucleotide. Active enzyme reacts with X creating an oligonucleotide decorated with product P, which allows capture of via a suitable receptor for P (e.g. anti-P antibody).
E: The substrates (X) for the enzyme of choice (white hexagon) are attached to a tag. Active enzyme reacts with X creating tagged product (white circle). Product reacts spontaneously with a suitable scavenger molecule attached to an oligonucleotide, which allows capture.
Figure 3E:
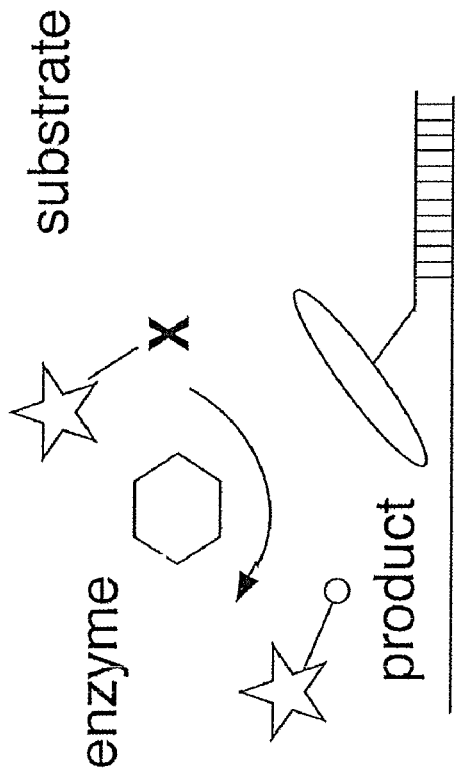
Figure 3E:
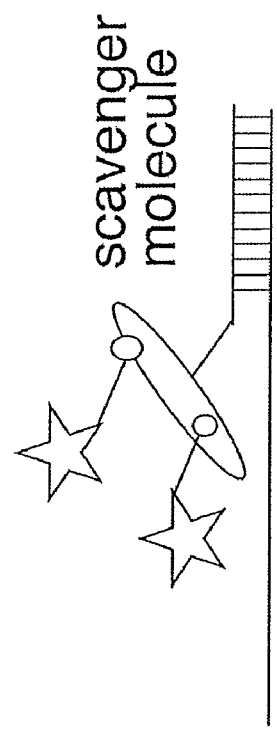
Figure 3D:
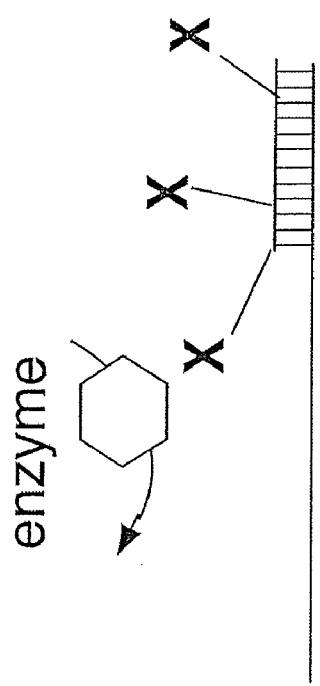
Figure 3D:
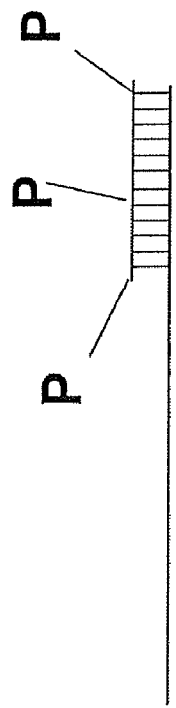
Figure 4A:
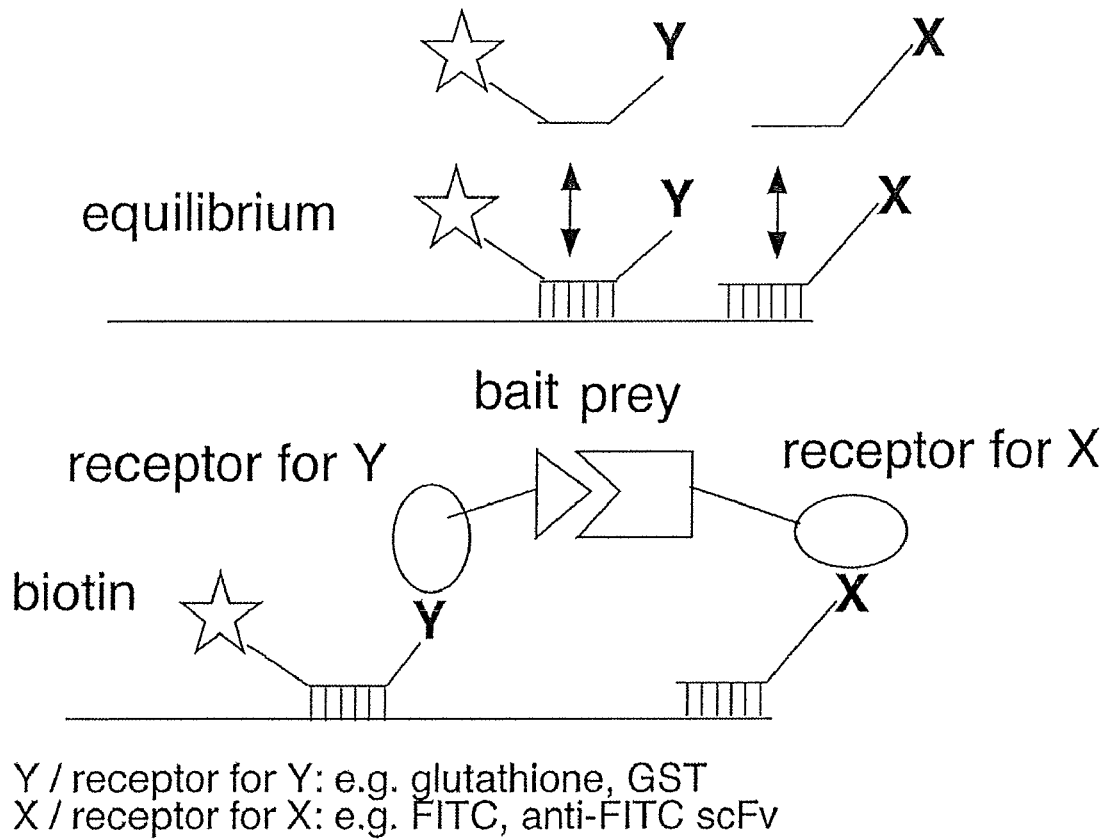
FIG. 4: CST selection for protein-protein interaction
Molecules (X & Y) for which there are suitable high affinity receptors (receptorY and receptor X) available are attached to the ends of two oligonucleotides, each of which is too short to stably hybridize to the plasmid on its own. One oligonucleotide (or both) bears a capture tag (e.g. biotin).
Figure 4B:
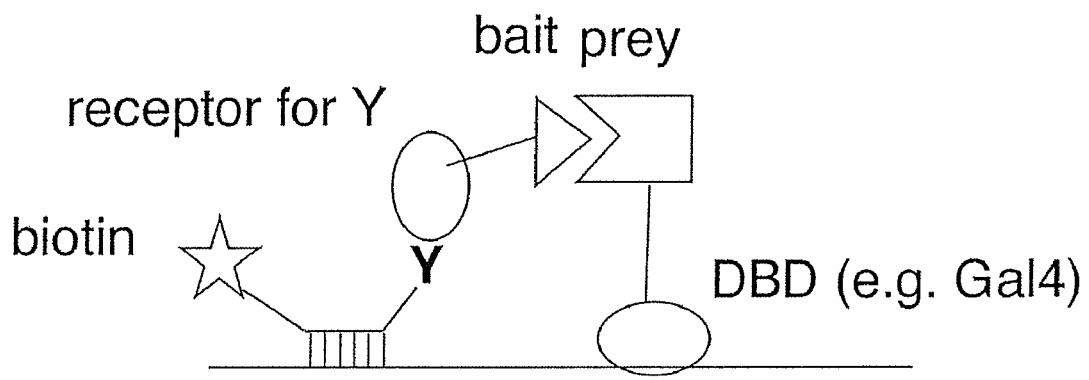

As shown in the examples, simple oligonucleotide hybridization to a target sequence provides sufficient stability for capture of the oligo-plasmid complex after extension Various technologies are available to increase the stability of the oligo-plasmid complex (FIG. 1) including sequences capable of triplex formation, the use of modified bases such as diaminopurine (to replace A), G-clamps (Matteucci 99), LNA (ref), INA (ref), hybrid oligonucleotides (Ishihara & Corey 99), including DNA-PNA or DNA-peptide hybrids (Corey) or UV crosslinking using psoralen (ref). Alternatively, the hybridizing oligonucleotide may be designed as a "padlock probe" (Landegren) with a defined sequence gap between the two "sticky feet". Extension, followed by ligation would generate a virtually non-dissociable oligo-plasmid catenane. (FIG. 2)

Duplex melting, strand invasion and hybridization may be facilitated through RecA or the use of so-called "PNA openers". For example RecA together with aS-ATP has been shown to promote the formation of a stable nucleoprotein complex with a single stranded biotinlylated probe and homologous sequences in circular double-stranded DNA (Hakvoort et al 96, Zhumabayeva et al 99), which can subsequently be captured on magnetic beads. This technology has been applied successfully for the isolation of cDNAs. Short homopyridine PNA oligomers are able to invade complementary sequences in duplex DNA yielding P-loops (Nielsen 91, Demidov 95) and these can act as artificial transcription promotors in linear duplex DNA (Mollegaard 94). All these strand opening reactions are facilitated by negative supercoiling in plasmid DNA but at least some are also applicable to non-supercoiled linear double-stranded DNA.

Those skilled in the art will appreciate that there may be other methods of achieving the same result.

Tag Capture.

Tag-specific capture of the plasmid-oligonucleotide complex requires discrimination of tag-modified complexes from unmodified complexes. Using appropriate washing conditions it may even be possible to discriminate degrees of tag incorporation.

Those skilled in the art will appreciate that the precise details of tag capture will depend upon the nature of the tag. For example, in the case that the capture tag is a product of the enzyme of interests catalysed reaction, then tag capture may be brought about using an antibody specific for the antibody. Conveniently, biotin-tagged complexes can be captured on streptavidin coated beads.

In all cases, it is important that during the washing process, required to remove untagged plasmid-oligonucleotide complexes, such complexes remain stable, i.e. the non-covalently associated plasmid and oligonucleotide do not dissociate. Washing conditions may be adjusted depending on the type of plasmid-oligonucleotide complex such that such complex is stabilized, e.g. low salt conditions in the case of PNA-DNA complexes.

Under appropriate conditions such complexes can be very stable and have i.a. allowed affinity capture and recovery of microbial DNA at femtomolar concentrations even in the presence of an excess of exogenous DNA (Chandler et al. 2000).

(B) Modulating the Efficiency of Plasmid Capture/Sensitivity of the Method

The present inventors have performed extensive experiments aimed at optimising conditions to improve the efficiency of plasmid capture and therefore enhancing the sensitivity of the technique. These experiments are described in detail in Examples 10 to 14 herein.

In particular the present inventors have found that the efficiency of plasmid capture may be increased using any one or more of the techniques in the list consisting of the following: by increasing the Tm of the oligonucleotide/plasmid hybrid; by extending the oligonucleotide by more than 3 bases; by the use of a linker more than 40 atoms long between the molecular tag and the oligonucleotide and by the use of a oliognucleotide more than 10 bases long.

More specifically, according to the experiments performed by the inventors, the efficiency of plasmid capture is increased by increasing the Tm of the oligonucleotide/plasmid hybrid using any bases in the list consisting of the following: LNA bases and other suitable base types.

Other suitable bases for use according to the methods of the invention include but are not limited to diaminopurine (to replace A), G-clamps (Matteucci 99), LNA (Jepsen et al (2004), *Oligonucleotides*, 14, 130), INA (Christensen & Pedersen (2002), *Nucleic Acid Res*, 30, 4918) or any other base or backbone modifications that increase the Tm. Other possibilities to increase Tm include hybrid oligonucleotides (Ishihara & Corey 99), including DNA-PNA or DNA-peptide hybrids or covalent crosslinking to the template strand using a psoralen molecule stably incorporated into the oligonucleotide The present inventors have also found that the efficiency of plasmid capture is increased by extending the oligonucleotide by more than 20 bases. Advantageously, the efficiency of plasmid capture is increased by extending the oligonucleotide by more than 50 bases or more than 100 bases.

Further the present inventors have found that the efficiency of plasmid capture is increased by the use of a linker more than 50 atoms long between the molecular tag and the oligonucleotide. Advantageously, the efficiency of plasmid capture is increased by the use of a linker more than 70 atoms long between the molecular tag and the oligonucleotide. Most advantageously, the efficiency of plasmid capture is increased by the use of a linker more than 100 atoms long between the molecular tag and the oligonucleotide.

Various aspects and embodiments of the present invention are illustrated in the following examples. It will be appreciated that modification of detail may be made without departing from the scope of the invention.

All documents mentioned in the text are incorporated by reference.

EXAMPLES

Example 1

Materials and Methods

DNA manipulation and protein expression: DNA manipulation was according to Sambrook unless specified otherwise. Taq polymerase, Taq Stoffel fragment, □422 Taq, 611FrS Taq were expressed from pASK75 as described previously (Ghadessy 01, MethMolBiol (manuscript attached)). *S. solfataricus* Dpo4 was amplified from pET22b: Dpo4 (kindly provided by Dr. R. Woodgate, NIH, USA) using primers 1 and 2, cloned Xba I/Sal I into pASK75 and transformed into RW392. For expression RW392 cells harbouring pASK: Dpo4 were grown to $OD_{600}$=0.8 in 2×TY/Amp (01 µg/ml)/1% glucose, induced by addition of anhydrotetracycline to 0.2 µg/ml final and expressed for 4 h at 37° C.

Emulsification: After expression cells were emulsified as described previously (Ghadessy et al 01, MethMolBiol (manuscript attached)).

Primer extension: in vitro: Plasmid (colE1, e.g. pUC or pASK75) (10 ng) was mixed with primer (10-100 pMs total), dNTP mix (250 µM (final) of each dNTP, supplemented with 40-10 µM (final) biotin-16-dUTP (Roche) and 2.5 U Taq DNA polymerase (HT biotechnology) in 1× Taq buffer (50 mM KCl, 10 mM Tris-HCl (pH9.0), 0.1% TritonX-100, 1.5 mM $MgCl_2$) and incubated 94° C. 5 min, 50° C. 5 min, 72° C. 10 sec-5 min. Alternatively 2×10$^8$ expressor cells (washed twice in 1× Taq buffer) were mixed with primer (10-100 pM), dNTP mix (250 µM (final) of each dNTP, supplemented with 40-10 µM (final) biotin-16-dUTP (Roche) in 1× Taq buffer (50 mM KCl, 10 mM Tris-HCl (pH9.0), 0.1% TritonX-100, 1.5 mM $MgCl_2$) and incubated 94° C. 5 min, 50° C. 5 min, 72° C. 10 sec-5 min.

Plasmid capture: Plasmid-oligonucleotide complexes (POC) were purified from the reaction mixture either by passage through a ChromaSpin1000 column (Clontech) according to manufacturer's instructions, purified with Qiagen PCR purification kit following the manufacturers instructions or preferably ethanol precipitated (3 v/v ethanol, 1/10 v/v 3M NaAc) in the presence of mussel glycogen (Roche) as a carrier and resuspended in an equal volume of bead binding buffer (BBB: 10 mM Tris pH 7.5, 1 mM EDTA, 0.2 M NaCl).

20 µL Dynabeads-280 (Dynal) were washed twice in BBB, blocked with 0.5% casein or 1 mg/ml BSA for 30 min at 22 C, added to POC in a total volume of 0.5 ml and incubated for 2 h on a overhead rotator at room temperature (RT). Beads were washed twice with BBB and twice with 10 mM Tris pH 8.0 (or for less stringent washing conditions twice with high salt BBB 10 mM Tris pH 7.5, 1 mM EDTA, 1 M NaCl and once with 10 mM Tris pH 8.0) and resuspended in 50 µl 10 mM Tris pH 8.0.

Plasmid detection by PCR: 1 µl Dynabeads was added directly to 200 PCR mix comprising primers 4 and 5 (amplifying the bla gene), all 4 dNTPs (at 250 µM final each) and 2.5 U of Taq 2.5 U Taq DNA polymerase (HT biotechnology) in 1× Taq buffer (50 mM KCl, 10 mM Tris-HCl (pH9.0), 0.1% TritonX-100, 1.5 mM $MgCl_2$) and cycled 94° C. 5 min, 15× (94° C. 15 sec, 50° C. 15 sec, 72° C. 1.5 min), 65° C. 2 min.

Plasmid detection by qPCR: the number of plasmid molecules captured on the Dynabeads was quantified using quantitative real-time PCR. Amplification of a short amplicon from the template plasmid was detected by measuring the fluorescence generated from incorporation of CybrGreen dye using Opticon 2 (GRI Molecular Biology Ltd). The conditions we used as recommended by manufacturer except for doubling of the concentration of the CybrGreen dye in the reaction mix. 1 mkl of Dynabeads was added directly to 20 mkl of PCR mix comprising primers qPCRf and qPCRx amplifying the 100 bp fragment of pASK75 plasmid, all 4dNTPs at 200 mkM each, and 2.5 U of SuperTaq DNA polymerase in 1× Taq buffer (HT biotechnology). We were able to reliably detect and discriminate between 10$^4$ and 10$^9$ plasmid copies.

Plasmid elution & transformation: For plasmid elution, beads were incubated in 200 µl bead elution buffer (BEB: 1 mM EDTA, 0.1M NaOH) for <5 min. Beads were captured on the magnet and the plasmid in the supernatant precipitated by the addition of 1/10 V of 3M NaAc, 3V of ethanol and mussel glycogen (Roche) as a carrier. The plasmid was precipitated by centrifugation in a bench top centrifuge, the pellet was washed once in 96% ethanol at RT, dried and resuspended in H2O and transformed by electroporation Plasmid detection from beads: Presence of plasmid bound to beads was detected by direct PCR amplification from beads using primers 4 and 5 using 1 µl beads as template and the following program: (94° C. 5 min, 17× (94° C. 15 sec, 50° C. 15 sec, 72° C. 1.5 min), 65° C. 2 min).

Oligonucleotide Primers:

1: 5?-CAG GAA ACA GCT ATG ACA AAT CTA GAT AAC GAG GGC AAA AAA TGA TTG TTC TTT TCG TTG ATT TTG AC-3?

2: 5?-GTA AAA CGA CGG CCA GTC GAC GCG GCC GCT TAA GTA TCG AAG AAC TTG TCT AAT CC-3?

3: 88fo2: 5'-ACC ACC GAA CTG CGG GTG ACG CCA AGC G-3'

4: Blaba: 5'-GCA CCA GGA TCC CTA AGG AGA TAT ACA TAT GAG TAT TCA ACA TTT CCG TGT C-3'

5: Blafo: 5'-GGG CTC GGC AGT CGA CTT ACC AAT GCT TAA TCA GTG AGG C-3'

6: 5'-GGC GAC TCT AGA TAA CGA GGG CAA AAA ATG CGT GGT ATG CTT CCT CTT TTT GAG CCC AAG GGC CGC GTC CTC CTG-3'

7: 5'-GCG GTG CGG AGT CGA CTC ACT CCT TGG CGG AGA GCC AGTC-3'

24G: 5'-AAG 5AT CTT CAC CTA GAT CCT-3' (based on oligo 24 from JACS (1999), 121, 2012-2020, 2 extra 5' AA, 5=G-clamp as in PNAS (1999), 96, 3513-3518 for increased Tm (kindly provided by S. Holmes, MRC LMB) but with 2' Ome)

24 GB: 5'-6 AAG 5AT CTT CAC CTA GAT CCT-3' (based on oligo 24 from JACS (1999), 121, 2012-2020, 2 extra 5' AA, 5=G-clamp as in PNAS (1999), 96, 3513-3518 for increased Tm (kindly provided by S. Holmes, MRC LMB) but with 2' Ome), 6=biotin 24DAP: 5'-C5A 5A5 GG5 TCT TCA CCT AGA TCC T-3' (based on oligo 24 from JACS (1999), 121, 2012-2020, extra 5' sequence CAAAAA, 5=2,6-diaminopurine for increased Tm 24DAPB: 5'-6 C5A 5A5 GG5 TCT TCA CCT AGA TCC T-3' (based on oligo 24 from JACS (1999), 121, 2012-2020, extra 5' sequence CAAAAA, 5=2,6-diaminopurine for increased Tm, 6=biotin 26DAP24B: 5'-6 GGT C5T G5G 5TT 5TC 5AA AAG GAT CTT CAC CTA GAT CCT-3' (based on oligo 24 from JACS (1999), 121, 2012-2020, extra 5' sequence, CAAAAAG-GATCTTCACCTAGATCCT, 5=2,6-diaminopurine for increased Tm, 6=biotin qPCRf 5'-AAGCCATACCAAACGACGAG-3' qPCRr 5'-TTGCCGGGAAGCTAGAGTAA-3' pASK2 5'-GATCTTCACCTAGATCCT-3' pASK3 5'-CATGCCATCCGTAAGATGC-3' pASK4 5'-GTTCCTGGCCTTTTGCTGG-3' pASK5 5'-ACGTAGTGGGCCATCG-3'

24LNA: 5'-GAT CTTCAC CTA GAT CCT-3' underlined bases were LNA (MRC oligoservice)24 5'-GAT CTT CAC CTA GAT CCT-3'

18B 5'-Biotin-108 atom linker-GATCTTCACCTAGATCCT-3'

| 18 | 5'GATCTTCACCTAGATCCT-3' |
| 14 | 5'TTCACCTAGATCCT-3' |
| 12 | 5'CACCTAGATCCT-3' |
| 10 | 5'CCTAGATCCT-3' |
| 8 | 5'TAGATCCT-3' |

Example 2

Figure 5A:
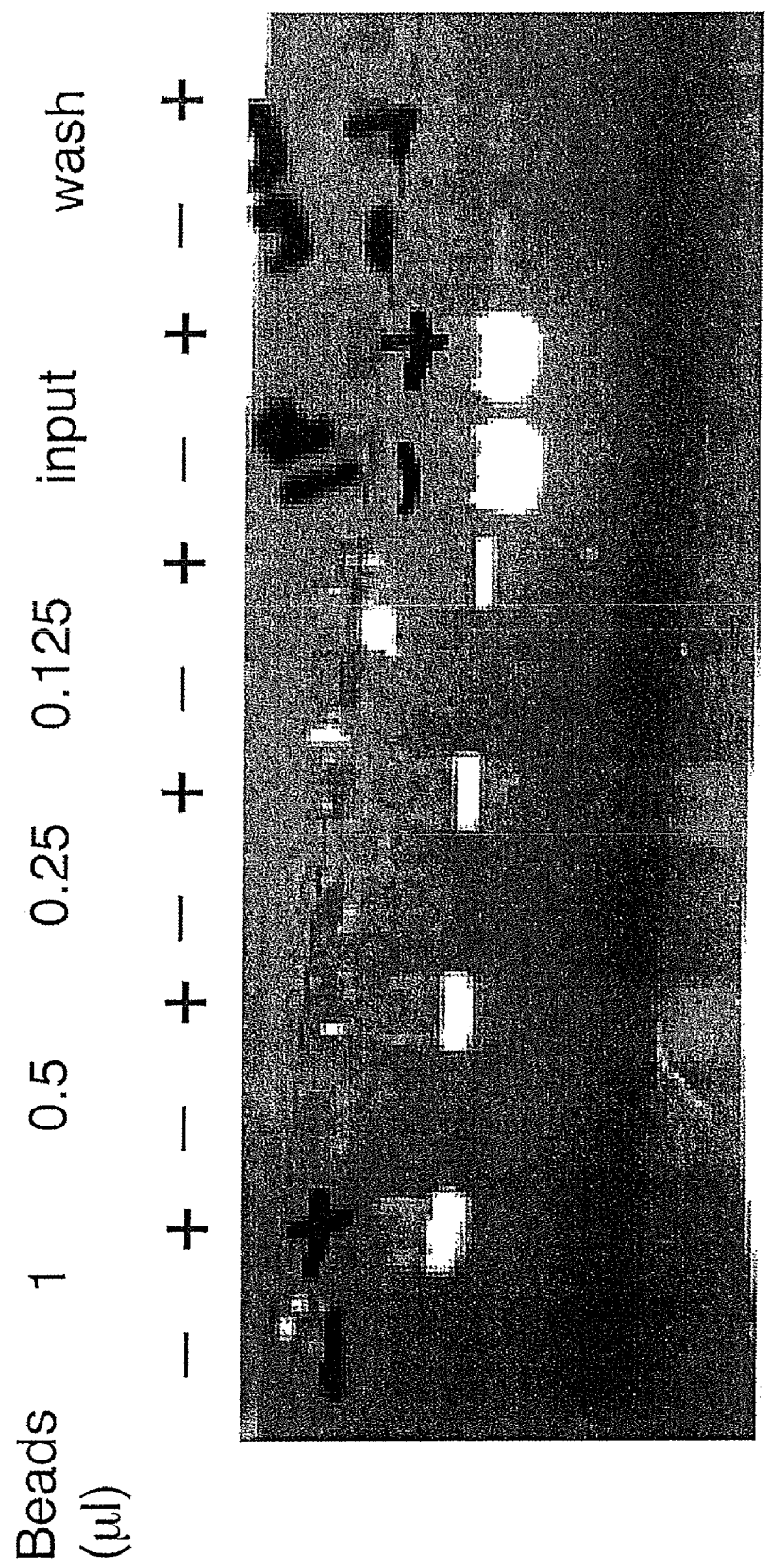
Figure 5B:
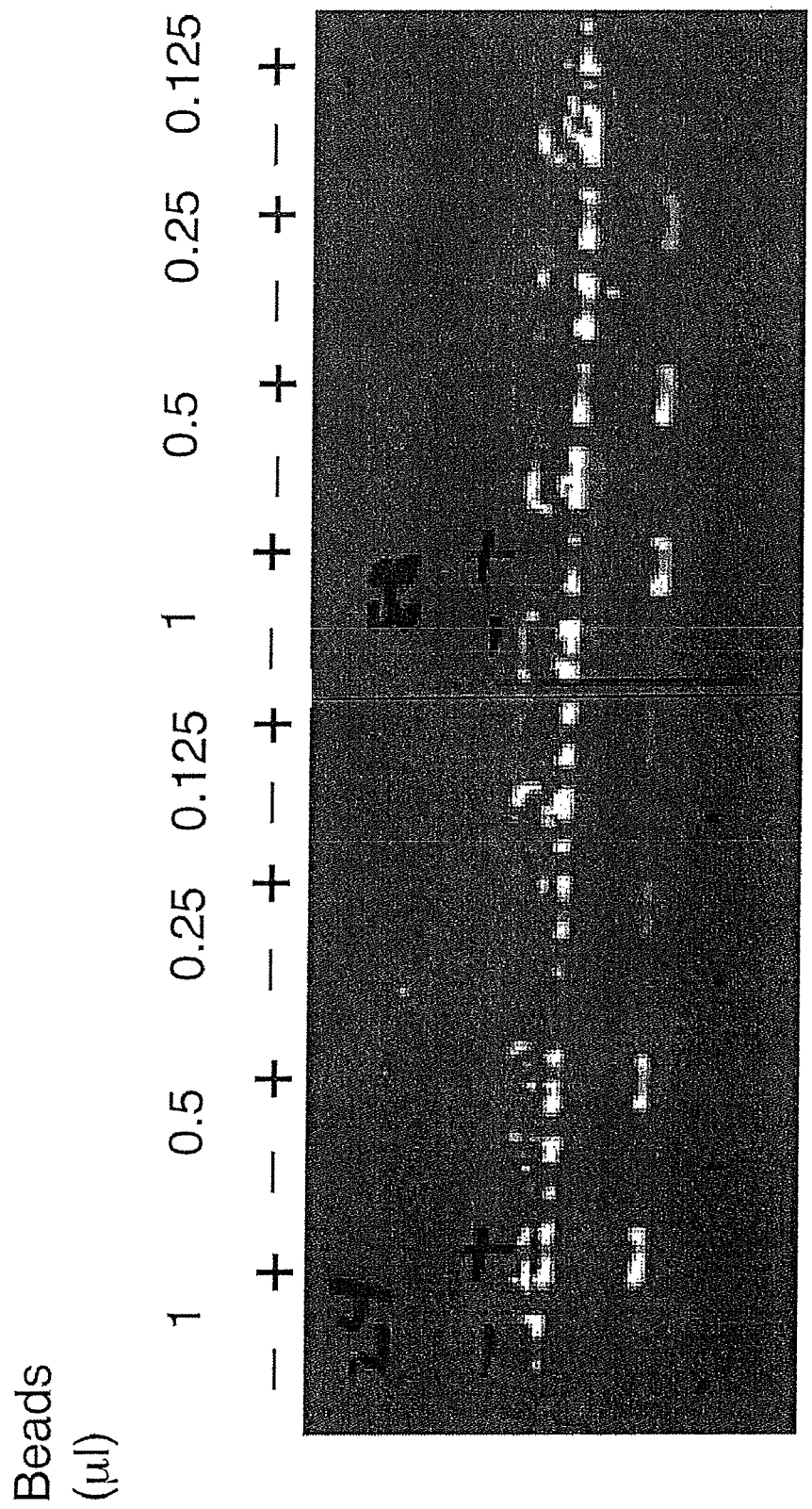

Activity Based Plasmid Capture Due to Incorporation of Biotin-16-dUTP 24G (or oligo 3) were used for in vitro primer extension on pUC119 plasmid using biotin-16-dUTP as the tag. Extensions were carried in the presence (+fraction) or absence (−fraction) of Taq polymerase. Plasmid-oligo complexes were purified on ChromaSpin1000, captured after extension on streptavidin coated magnetic beads and the presence of captured plasmid on the beads was determined using PCR from the beads (FIG. 5A). As can be seen only in the presence of an active polymerase does plasmid get captured on the beads, while the wash contains plasmid both in the presence and absence of polymerase. Comparison of two different primers (24G vs oligo 3 (88)) both of which prime on pASK showed little difference in the efficiency of capture (FIG. 5B), despite the fact that oligo 24 had previously been identified as being especially potent at strand invasion (Ishihara & Corey, 99).

Plasmid was also detected by elution from the beads and retransformation (Table 1)

| +polymerase | −polymerase |
|---|---|
| 113 colonies | 23 colonies |

Although disappointing in yield, there is a clear (approx. 5-fold) difference in the amount of plasmid eluted.

Example 3

Plasmid is Captured and Extension Product is not Captured

The experiment in example 2 was repeated, but in order to show that PCR amplification from the beads did actually detect captured plasmid and not simply the production and capture of biotinylated extension products, beads were incubated with 20 U DpnI (New England Biolabs) for 2 h at 37° C., prior to amplification. DpnI only digest methylated DNA, therefore selectively destroys plasmid DNA but not extension products. As can be seen from FIG. 6, predigestion with DpnI drastically reduces the amount of PCR product obtained indicating that the PCR detects captured plasmid and not captured extension products.

Example 4

Plasmid Capture from Cells

The capture experiment was repeated using bacterial cells expressing active Taq polymerase from pASK as opposed to using recombinant Taq polymerase and extraneously added pASK plasmid. Experiments were carried out in the presence (+ fraction) or absence (− fraction) of the dNTP mixture. As before only when polymerase can extend and tag the hybridized oligonucleotide is there capture (FIG. 7). Significantly, plasmid capture from cells appears to be nearly as efficient as plasmid capture from solution indicating that the initial heating step is sufficient to liberate plasmid from the cell (FIG. 7). PCR analysis of the bead washes indicates that although large amounts of plasmid initially adhere to the beads in a non-specific way, these can be washed off if non-tagged (as can be seen from the larger amount of plasmid present in the washes from the − fraction).

Example 5

Plasmid Capture from Cells in Emulsion

The experiment of example 5 was repeated but using emulsification of the extension reaction comprising expressor cells, oligonucleotide 24G, dNTP mix including biotin-16-dUTP in 1× Taq buffer. Again only when polymerase can extend and tag the hybridized oligonucleotide is there capture (FIG. 8).

Example 6

Polymerases with Low Processivity or Activity can be Captured Efficiently Using CST.

The capture experiment of example 5 (was repeated using bacterial cells expressing different polymerases with variable activities ($V_{max}/K_M$) or processivities. These included Taq polymerase (high activity, high processivity), Taq Stoffel fragment (high activity, low processivity), Taq □442 (low activity, low processivity, low stability), Taq 611 (inactive), Taq611+ (Taq611 with recombinant Taq added) and *S. solfataricus* P2 Dpo4 (medium activity, medium to low processivity).

PCR analysis of plasmid capture shows that CST allows efficient capture of Taq (FIG. 9A, 9B) and Dpo4 (FIG. 9B) and to a lesser extent the Stoffel fragment (FIGS. 9A, 9B), while Taq □442 (FIGS. 9A, 9B) or the inactive Taq611 (FIG. 9A) are not captured. Taq611+ (Taq611 with recombinant Taq added (FIG. 9A)) is efficiently captured proving that the differences in capture are not due to differences in the polymerase gene sequences but due to the activity and processivities of the encoded polymerases.

Example 7

Selection of Active Polymerases Using CST

In order to determine if CST could be used to select for polymerase activity from a repertoire of clones, cells expressing active Taq wt polymerase were spiked into an excess ($10^2$-fold, $10^3$-fold, $10^4$-fold. and $10^6$-fold) of cells expressing inactive Taq 611 polymerase emulsified and CST selection carried out. Captured plasmid composition was analyzed using PCR from the beads.

For the $10^2$- and $10^3$-spike, only the 611 region was amplified before and after selection and Taqwt and 611Taq distinguished by restriction digest (Taq611 has a Bgl II restriction site missing in the Taq wt enzyme). As can be seen from FIG. 10A, there is clear enrichment in both the $10^2$- and $10^3$-spike as is evident in the appearance of a Bgl II resistant fraction after selection.

Figure 10B:
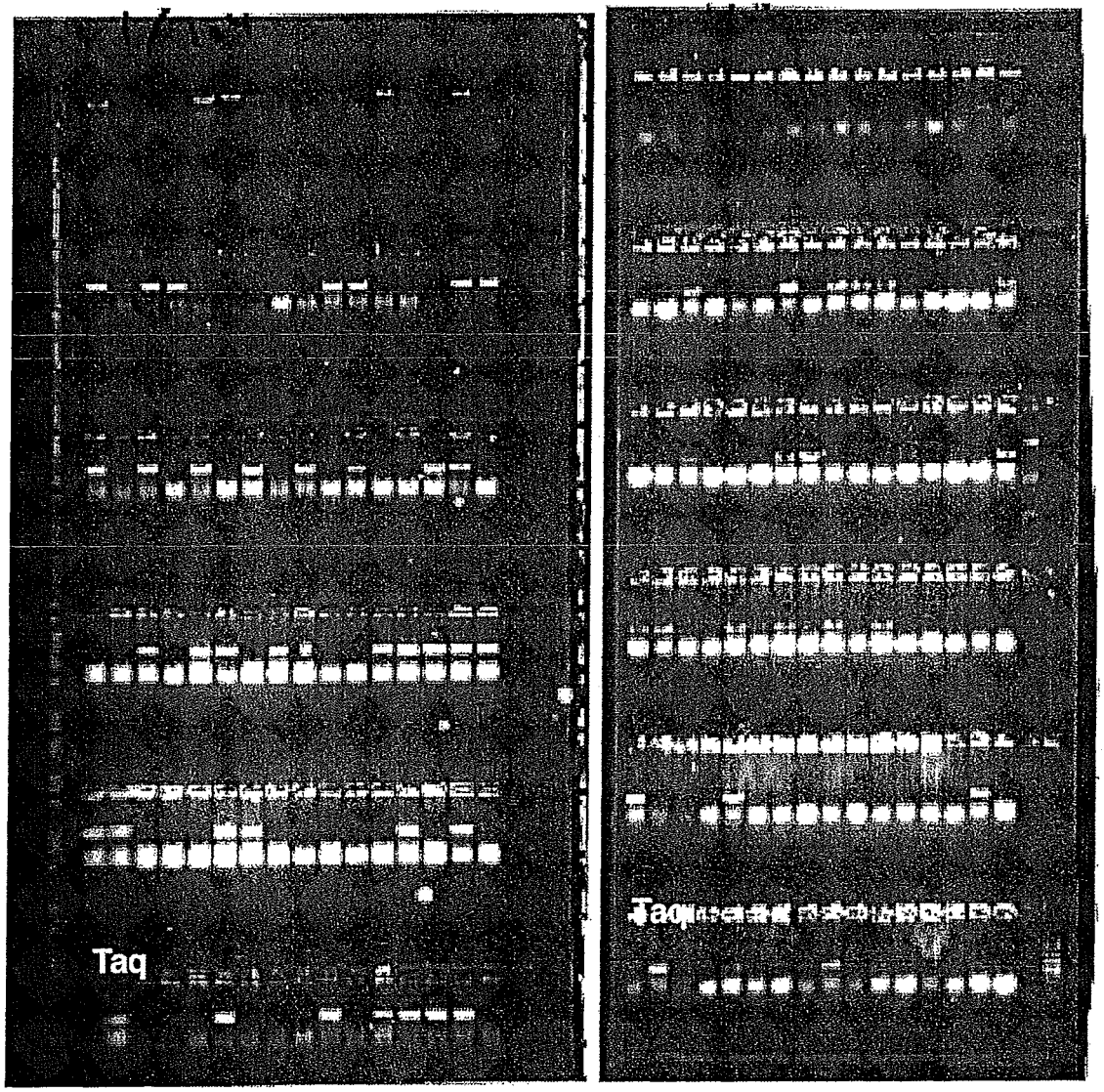

For the $10^4$- and $10^6$-spike, the whole Taq polymerase gene was amplified using primers 6, 7 from the beads and recloned Xba I/Sal I into pASK for expression after which 100 clones were scored for activity. As shown in FIG. 10B, there were 47/95 active clones after selection for the $10^4$-spike and 21/95 active clones after selection for the $10^6$-spike, indicating a selection factor of >$10^4$-fold.

Example 8

Discrimination of Polymerase Substrate Specificity Using CST

In order to assess if CST could discriminate between distinct polymerase activities regarding extension or incorporation of unnatural substrates, CST experiments were carried as in example 2 using recombinant Taq, as well as recombinant Taq mutants M1 and R22. M1 has an increased ability to extend the hydrophobic base analogue 5-nitroindole, while R22 has an increased ability to incorporate ribonucleotides. As FIG. 11 shows, M1 displays an increased ability to extend from primer 3 bearing a 3' analogue 5-nitroindole, while R22 shows much increased, although weak capture when extension is carried in an nucleotide mixture in which dAIP is entirely replaced by ATP (equimolar).

Example 9

Simple Hybridization of Biotinylated Oligonucleotides to Plasmid can be Sufficient for Capture The capture of the plasmid by use of an oligonucleotide with a 5' biotin was compared to the plasmid capture by identical non-biotinilated oligonucleotide. In contrast to example 2, simple hybridization (incubation at 95 C for 5 min, annealing at 50 C for 5 min) of 10 pM oligo and 10 fM plasmid pASK75 showed capture of the $10^7$ copies of plasmid with the biotinilated oligonucleotide, while only about $10^5$ copies of the plasmid were captured on magnetic beads non-specifically when non-biotinilated oligonucleotide was used (FIG. 12). This is due to the use of a high-salt work up of plasmid-oligonucleotide complexes (Qiagen PCR prep kit) rather than a low-salt work-up (ChromaSpin). In a typical experiment a starting number of plasmids is about $10^8$ copies and about 5-10% of those can be recovered by binding to the beads.

Note: the DNA oligonucleotide used in this experiment (24G) is stabilized by inclusion of a G-clamp.

It can be concluded that a single biotin is sufficient for capture on Dynabeads.

Example 10

Comparison of DNA Oligonucleotides and DNA-LNA Oligonucleotides

Oligonucleotides containing 5' biotin and about 30% LNA bases (which lead to increased Tm of a primer-template hybrid) were tested in vitro for plasmid capture. It was found that increased stability of the LNA primer-plasmid complex led to about 5-50 fold increase in the plasmid capture by hybridization (with no extension) when compared to the all DNA oligonucleotides (with or without G-clamp) (FIGS. 11, 12). The increase is larger when compared to a standard all DNA oligonucleotide 24, FIG. 12), than when compared to a modified DNA oligonucleotide 24G (FIG. 11).

Example 11

Effect of the Extension Length on Plasmid Capture

A 5' biotinylated DNA (24) or DNA-LNA oligonucleotide (24LNA: 5'-GAT CTT CAC CTA GAT CCT-3', underlined nucleotides LNA) were extended in vitro by 3, 9 or hundreds of bases and plasmid capture was compared with that of a simple hybridization. Limited extension was possible using primer 24 and 24 LNA, which prime to replicate the template sequence: 3'-AAATTTGATCACTTC-5') and supplying either only dTTP (which limits extension to three bases (template sequence 3'-AAATTTGATCACTTC-5, templates bases in bold) or dTTP, dATP, dCTP (9 nucleotides, (template sequence 3'-AAATTTGATCACTTC-5', templates bases in bold)) or all 4 dNTPs (unlimited extension, hundreds of bases extension).

It was found that for DNA oligonucleotide there is a correlation between extension length and plasmid capture (the longer the extension, the more plasmid is captured, FIG. 13B), while for DNA-LNA oligonucleotide extension by 3 or 9 bases does not lead to significant increase in plasmid capture compared to simple hybridization (FIG. 13A). Unlimited extension however leads to an increase in amount of plasmid being captured on Dynabeads, These results provide a proof that in the CST selection improved catalytic efficiency of the polymerase (and, therefore, longer extension of the primer) leads to increased probability of the plasmid being captured. In this case, the DNA primer used did not have a G-clamp and therefore the difference between LNA/DNA and only DNA primer at no extension is closer to 50 fold rather than 5 fold as for 24G in example 11.

Example 12

Comparison of Different Primers for Use in CST

Primers that prime in different regions of pASK75 (24G, pASK2 5'-GATCTTCACCTAGATCCT-3', pASK3 5'-CATGCCATCCGTAAGATGC-3', pASK4 5'-GTTCCTGGC-CTTTTGCTGG-3' and pASK5 5'-ACGTAGTGGGC-CATCG-3') were compared in their efficiency of plasmid capture. As already seen in example 2, there was little difference in the efficiency of plasmid capture depending on the sequence or location of the primer (data not shown).

This result suggests that in CST selection parameters (e.g. sequence to be replicated) can be freely chosen.

Use of a mix of 5 primers (with the same final concentration (100 pM)) led to about 2-3 fold increase in the amount of plasmid being captured on the beads, which suggests that all of the plasmid is available for priming, and plasmid tagging can be achieved at multiple sites.

Example 13

Improving the Sensitivity of the CST

The efficiency of biotin capture and thus the sensitivity of the CST selection can be improved up to 100 fold with the use of a very long linker between the biotin molecule and the primer as previously suggested by hybridization experiments (Shchepinov et al., *NAR*, Vol 25, Issue 6, 1997). This document is herein incorporated by reference. In a test experiment efficiency of plasmid capture with 24 GB and 108B primers was compared. 108B primer has 5' biotin at a 108 atom long linker, while 24 GB primer has 5' biotin at 16-atom long linker. The efficiency of the plasmid capture after a simple hybridisation experiment (as in example 11) was up to 100-fold higher when 108B primer was used (FIG. 14).

Example 14

The Minimal Length of the DNA Primer Required for Capture 18 (5'GATCTTCACCTAGATCCT-3'), 14 (5'TTCAC-CTAGATCCT-3') 12 (5'CACCTAGATCCT-3'), 10 (5'CCTA-GATCCT-3') and 8 (5'TAGATCCT-3') primers of 18, 14, 12, 10 and 8 by length respectively, were tested in vitro for the efficiency of the plasmid capture after extension with dNTPs. It was noted that the length of the primer did not affect the efficiency of the plasmid capture so long as the primer/oligonucleotide was more than 10 bases long (FIG. 15)

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry, molecular biology and biotechnology or related fields are intended to be within the scope of the following claims.

The invention claimed is:

1. A method for the selection of an enzyme capable of modifying an oligonucleotide wherein the method is not dependent on the replication of the oligonucleotide modifying enzyme encoding gene, which method comprises the steps of:
  (a) providing one or more parent nucleic acids encoding one or more enzymes of interest, wherein the parent nucleic acid comprises the gene sequence of the selected enzyme(s) of interest;
  (b) compartmentalizing said parent nucleic acids according to step (a), such that each compartment comprises a parent nucleic acid together with the one or more enzymes encoded by the parent nucleic acid and an oligonucleotide specific for a region on the parent nucleic acid according to step (a), which oligonucleotide bears a capture tag;
  (c) providing conditions that permit the specific hybridization of the oligonucleotide of step (b) with a region on the parent nucleic acid;
  (d) providing conditions that permit 5' or 3' extension of the oligonucleotide of step (b) by the enzyme encoded by the parent nucleic acid to form an oligonucleotide extension product/parent nucleic acid complex by which the parent nucleic acid may be subsequently captured; and
  (e) capturing the oligonucleotide extension product/parent nucleic acid complex.

2. The method of claim 1 wherein, under the selection conditions, the method selects an enzyme having a property selected from the group consisting of: low catalytic turnover, low processivity, and the incorporation of modified substrates which generate a nucleic acid-like polymer that cannot be reamplified.

3. The method of claim 1 wherein said enzyme is selected from the group consisting of: polY family DNA polymerases, polX family DNA polymerases, and low processivity variants of high processivity polymerases.

4. A method for the selection of an enzyme capable of modifying an oligonucleotide wherein the method is not dependent on the replication of the oligonucleotide modifying enzyme encoding gene, which method comprises the steps of:
  (a) providing one or more parent nucleic acids encoding one or more enzymes of interest, wherein the parent nucleic acid comprises the gene sequence of the selected enzyme of interest;
  (b) compartmentalizing said parent nucleic acids according to step (a), such that each compartment comprises a parent nucleic acid together with the one or more enzymes encoded by the parent nucleic acid and an oligonucleotide specific for a region on the parent nucleic acid according to step (a), which oligonucleotide bears a capture tag;
  (c) providing conditions that permit the specific hybridization of the oligonucleotide of step (b) with a region on the parent nucleic acid;
  (d) providing conditions that permit 5' or 3' extension of the oligonucleotide of step (b) by the enzyme encoded by the parent nucleic acid to form an oligonucleotide extension product/parent nucleic acid complex by which the parent nucleic acid may be subsequently captured; and
  (e) capturing the oligonucleotide extension product/parent nucleic acid complex using a capture tag binding agent attached to a solid support.

5. The method according to claim 1, wherein said one or more parent nucleic acids are plasmids.

* * * * *